United States Patent

Mucciardi et al.

[11] 4,052,889
[45] Oct. 11, 1977

[54] SYSTEM FOR MEASUREMENT OF SUBSURFACE FATIGUE CRACK SIZE

[75] Inventors: Anthony N. Mucciardi, Silver Spring, Md.; Ramesh Shankar, Reston, Va.

[73] Assignee: Adaptronics, Inc., McLean, Va.

[21] Appl. No.: 694,546

[22] Filed: June 10, 1976

[51] Int. Cl.$^2$ .......................................... G01N 29/00
[52] U.S. Cl. ................................................. 73/67.8 S
[58] Field of Search ............... 73/67, 67.1, 67.2, 67.3, 73/67.8 R, 67.8 S

[56] References Cited

U.S. PATENT DOCUMENTS 3,924,456  12/1975  Vahaviolos ........................... 73/67
3,961,522  6/1976  Kilen ................................... 73/67

Primary Examiner—Jerry W. Myracle
Attorney, Agent, or Firm—Jay M. Cantor

[57] ABSTRACT

A system for detecting and measuring subsurface fatigue cracks wherein acoustic pulse-echo data from the crack under test are manipulated to extract all acoustic characteristics by means of a Fourier operation, deconvolution and inverse Fourier operation, providing a spectral and cepstral analysis on these data and then utilizing the results of the spectral and cepstral analysis to obtain parameters which are utilized in an adaptive learning network to provide crack length measurements.

24 Claims, 22 Drawing Figures

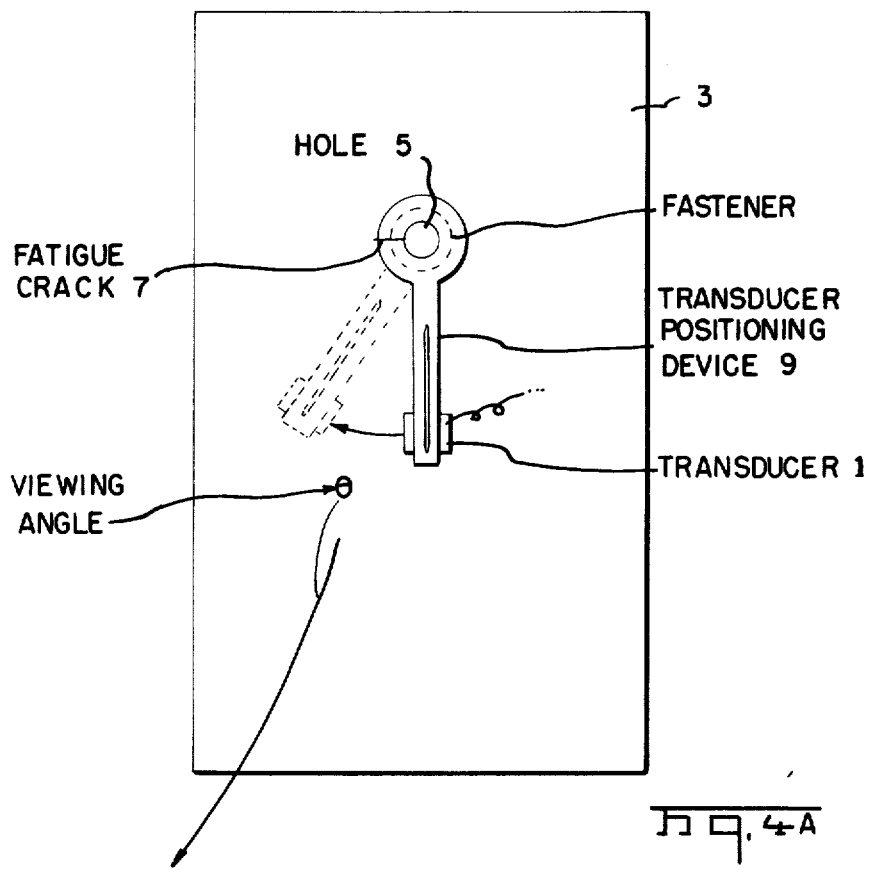
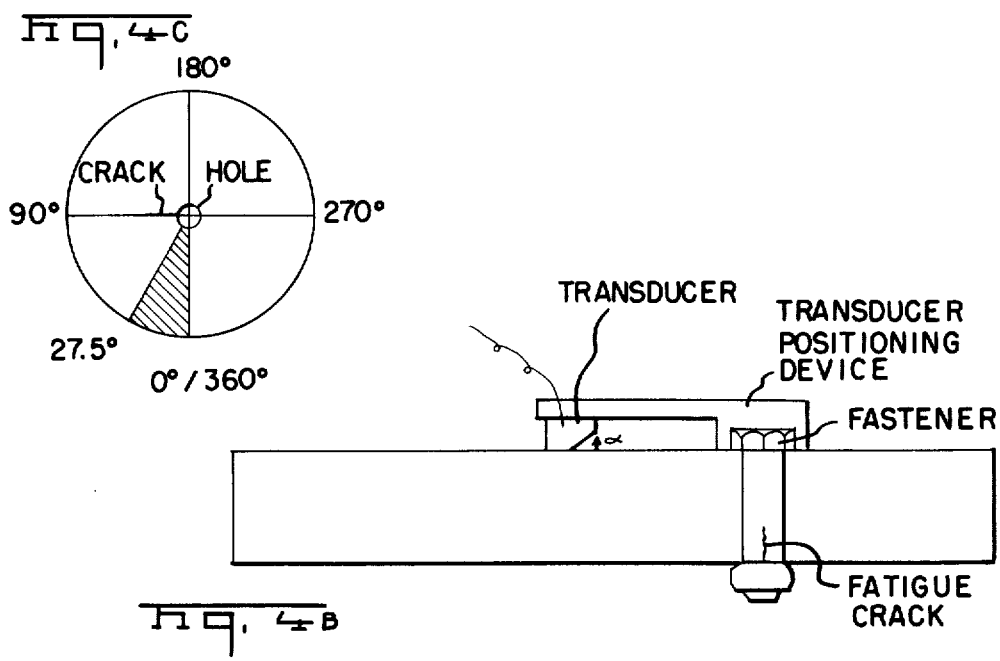

A = RESPONSE FROM HOLE
B = TIME BETWEEN RESPONSES FROM HOLE AND CRACK
C = RESPONSE FROM CRACK

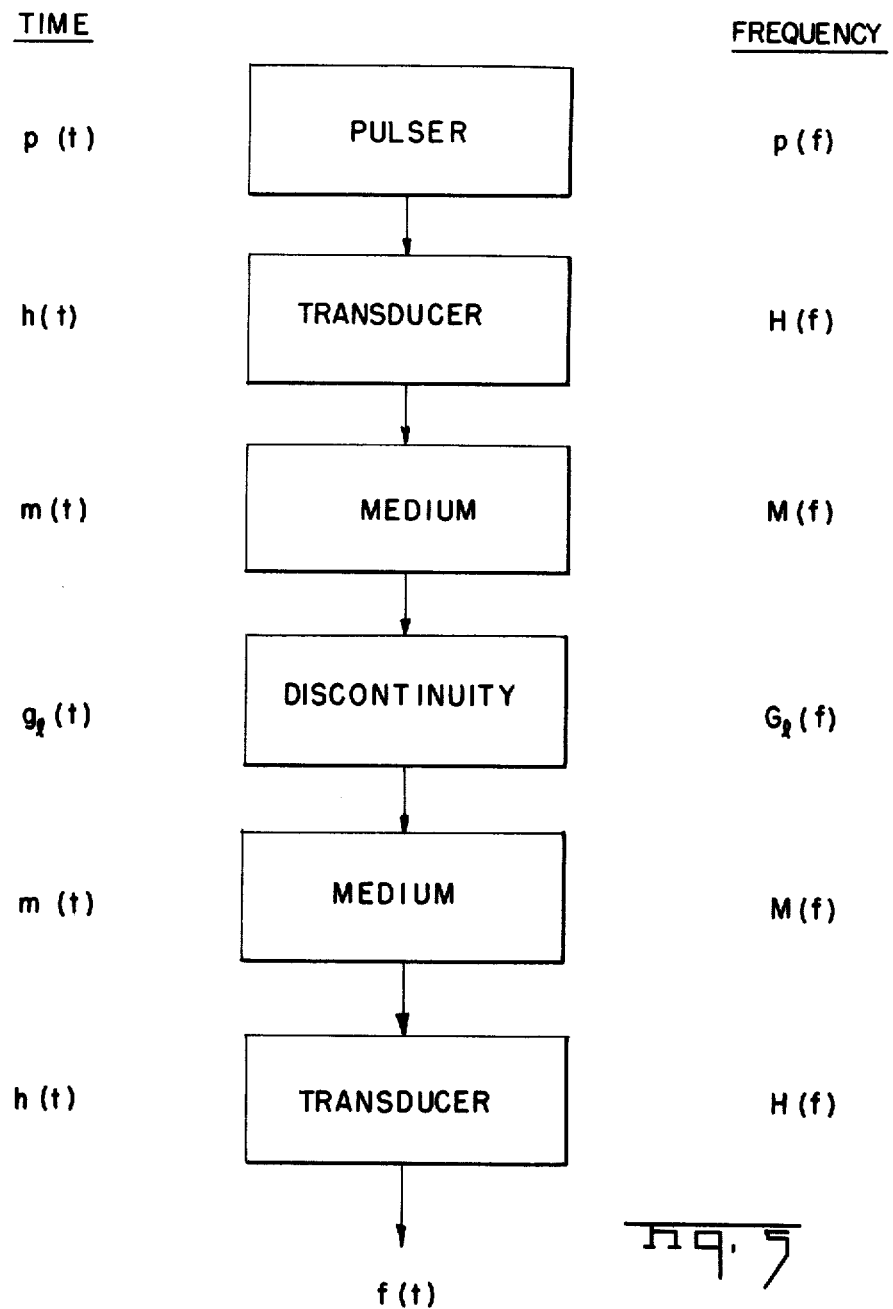

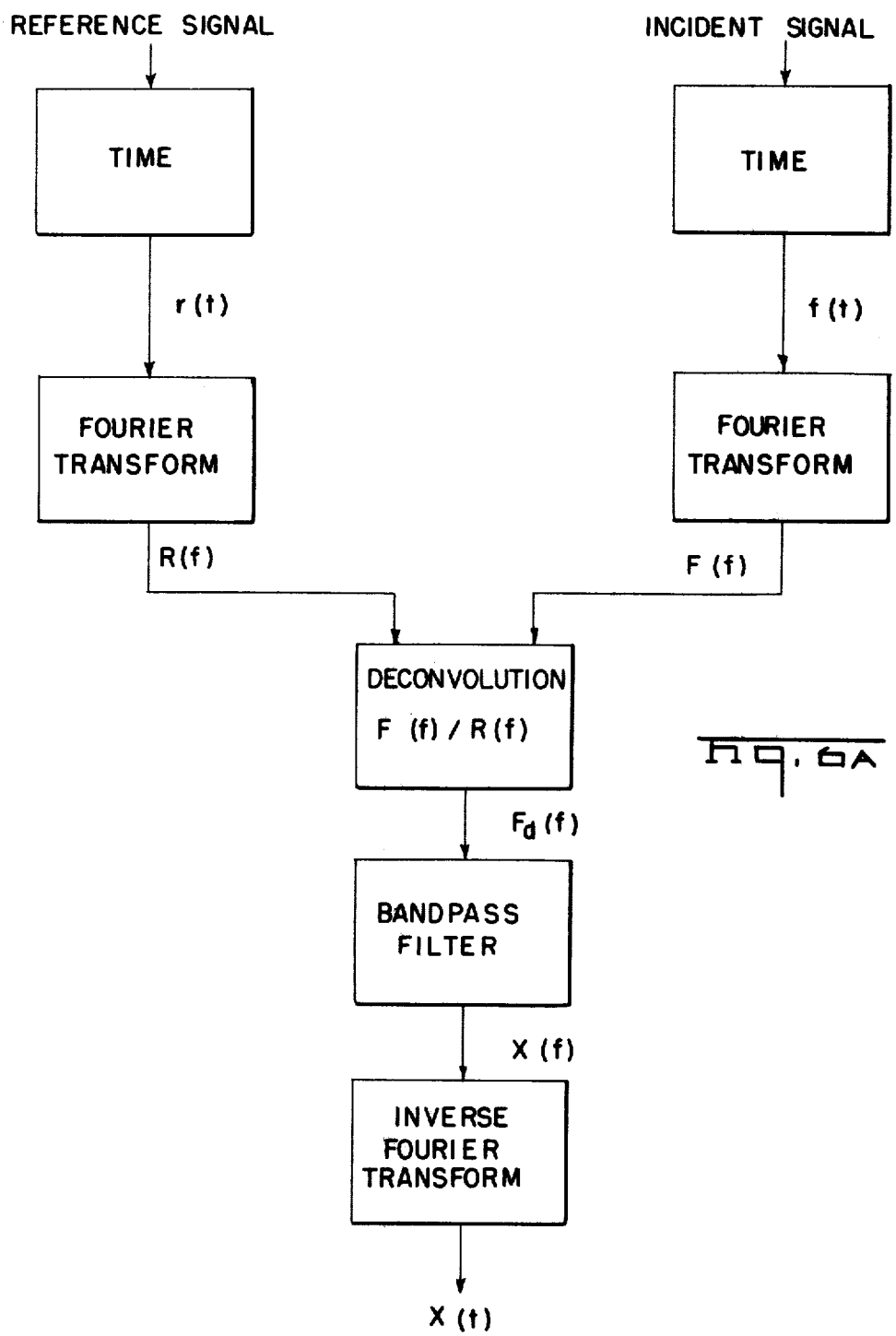

(a) CRACK RESPONSE FOR IDEAL TRANSDUCER
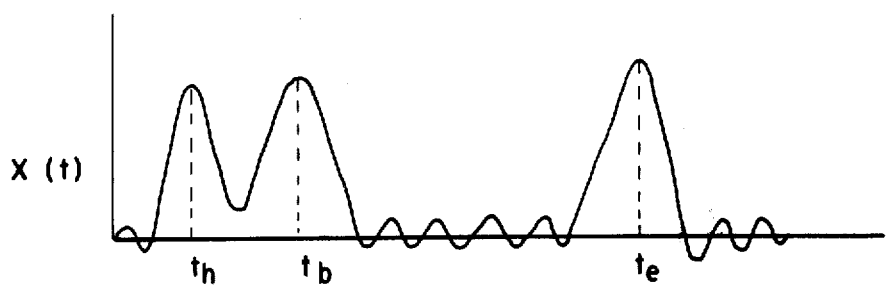
(b) RESPONSE FOR BAND-LIMITED TRANSDUCER
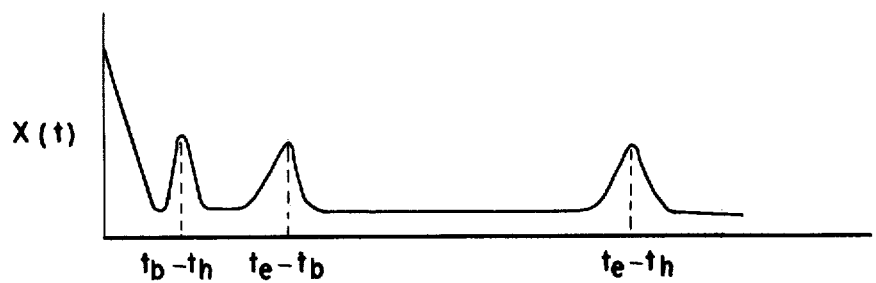
(c) CEPSTRUM OF RESPONSE OF BAND-LIMITED TRANSDUCER
Fig. 7

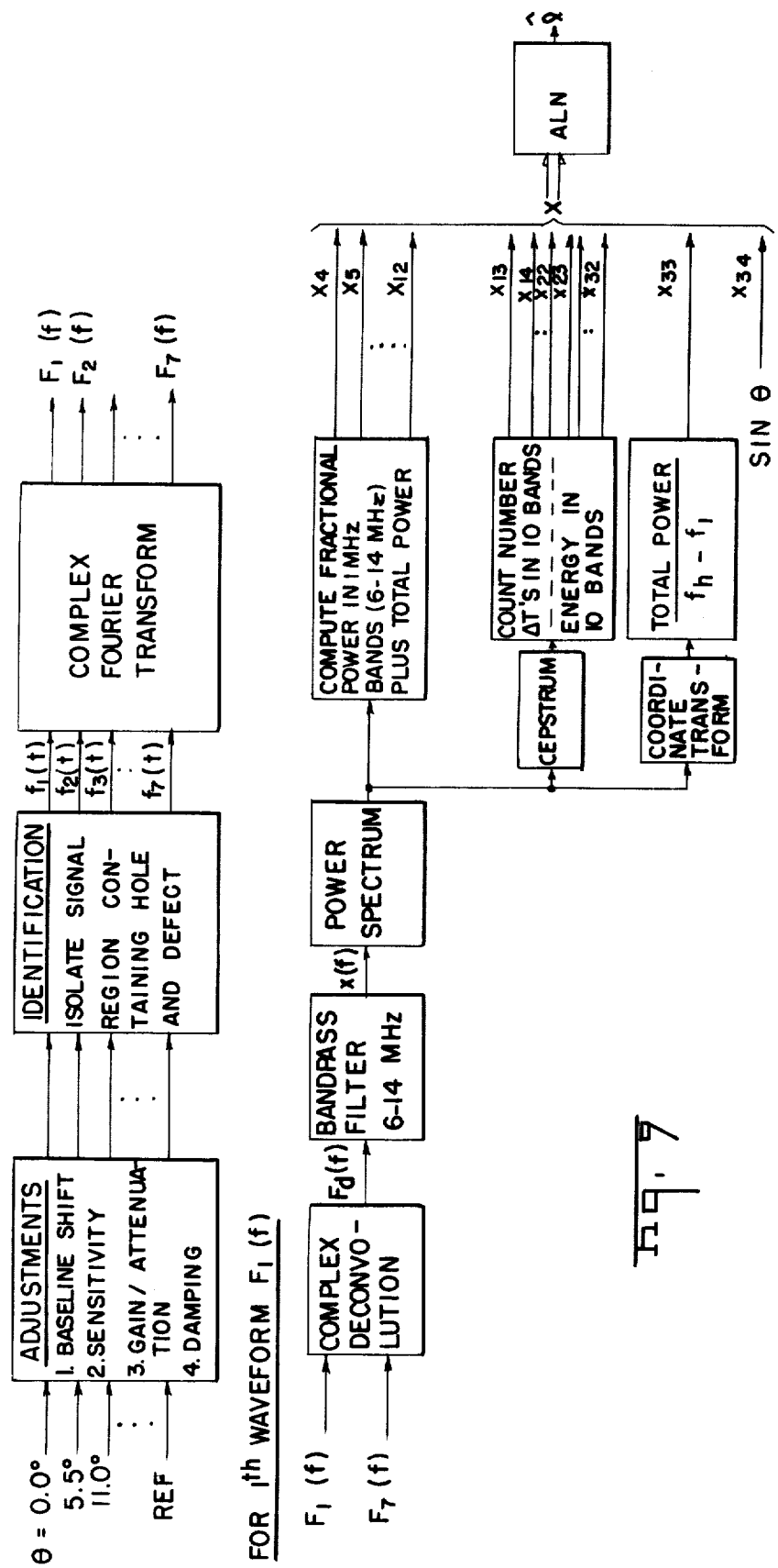

(a) MODEL SYNTHESIS
INPUTS = NDE WAVEFORM PARAMETERS = $X_1, \ldots, X_N$, SIN $\theta$
OUTPUT = $Y = L_N \left[ \dfrac{\ell(1-\sin\theta)}{30} \right]$
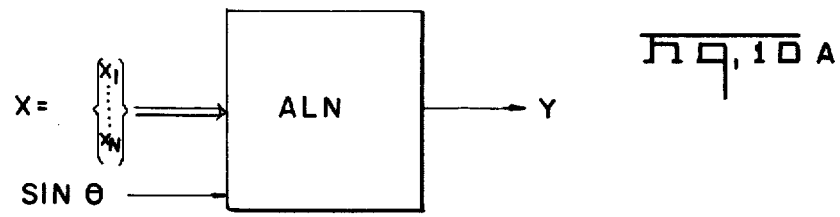
Fig. 10A
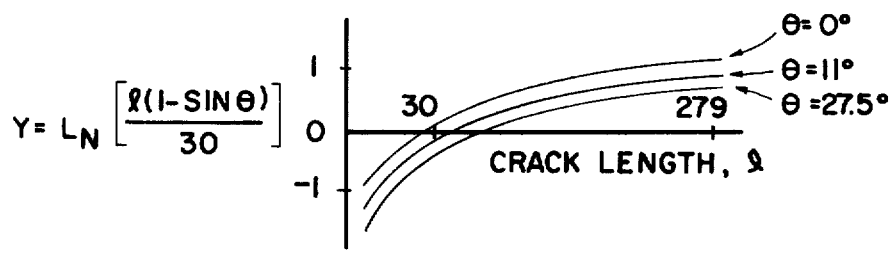
(b) MODEL USAGE
INPUTS = NDE WAVEFORM PARAMETERS = $X_1, \ldots, X_N$, SIN $\theta$
OUTPUT = $\hat{\ell}$ = ESTIMATED CRACK LENGTH
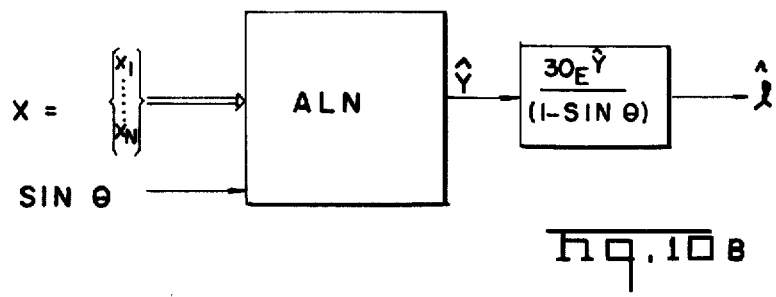
Fig. 10B

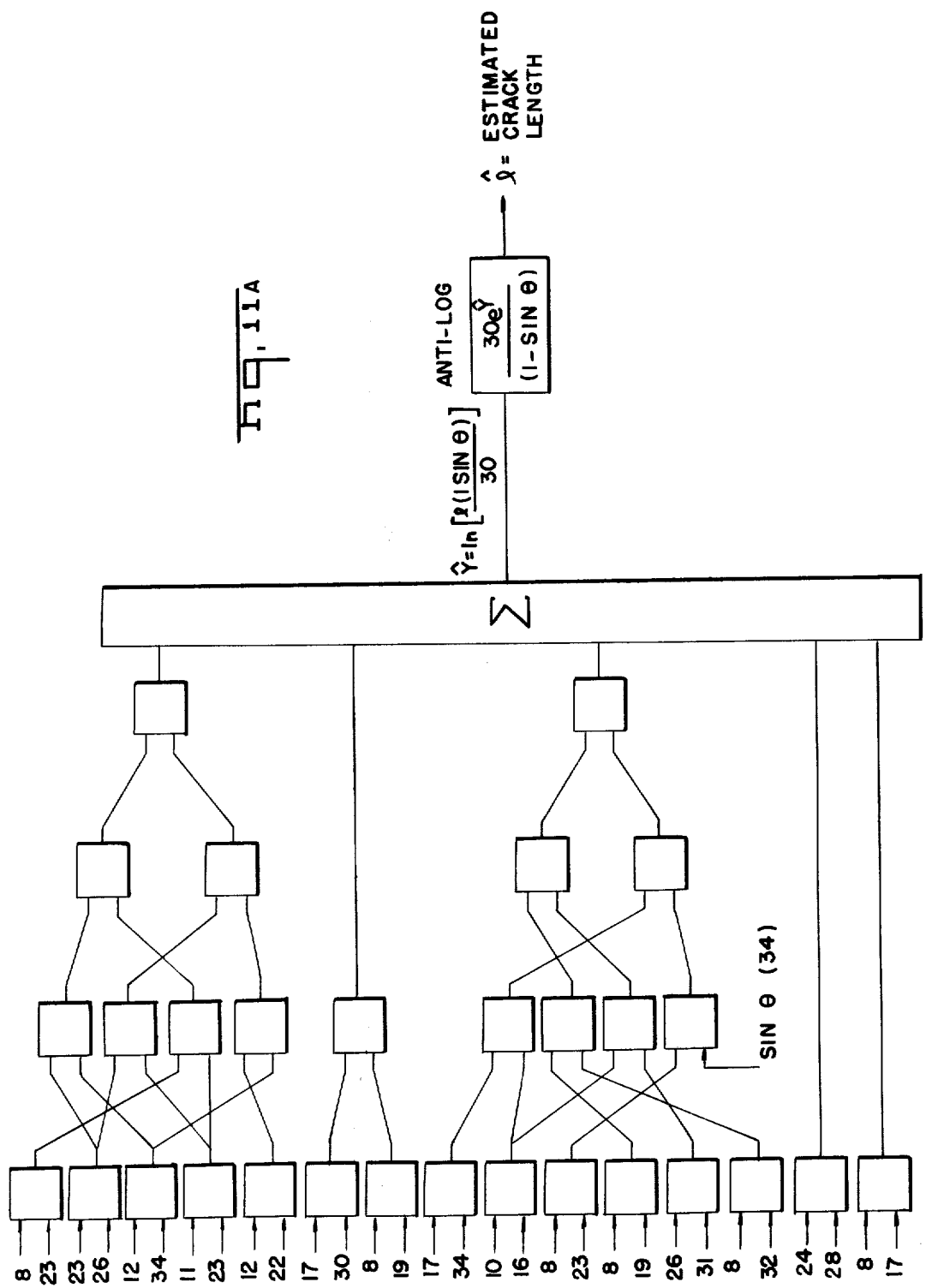

SYSTEM FOR MEASUREMENT OF SUBSURFACE FATIGUE CRACK SIZE

This invention relates to a system for detection and measurement of subsurface fatigue cracks and, more specifically, to a system of nondestructive detection and quantitative measurement of subsurface cracks in the range of about 0 to 270 mils to within about 70 percent of their nominally characterized length.

The identification of subsurface fatigue cracks is an important and difficult problem in the nondestructive evaluation of materials. Such cracks are induced around fastener holes in materials and are known to grow rapidly if the shearing forces on the material exceed a certain threshold. Thus, it is important to identify fatigue cracks on aircraft parts, turbine blades, etc. to develop suitable countermeasures to increase the realizability of these systems.

The Adaptive Learning Network (ALN) synthesized from nondestructive evaluation (NDE) waveform parameters inputs of the present invention is capable of detecting and measuring quantitatively subsurface fatigue cracks in the size range of about 0 to about 279 mils to within 70 percent of their nominally characterized lengths. Prior art investigations had achieved a 50 percent detection rate for cracks larger than 30 mils, and no detection capability for cracks smaller than 30 mils. However, the ALN fatigue crack measurement system herein is the first known fatigue crack NDE system capable of detection and measurement for this wide range.

Modern techniques for detection of subsurface fatigue cracks in metals rely on the analyses of reflected ultrasonic signals from such defects. The procedure involves directing a beam of ultrasound from an electronic pulser and transducer (which converts electrical pulses to ultrasound) towards the defect and capturing the return signal. The absence of a return signal within a prescribed time interval, that is determined by the velocity of ultrasound in the material and the material thickness, indicates an absence of a defect. The defect acts as a discontinuity to the ultrasound beam and a fraction of its energy is reflected back to the transducer. The return signal constitutes a defect "signature." Assumptions usually made about the defect signature include:

The larger the defect, the larger the signal amplitude,
The frequency spectrum of the return signal has essentially the same characteristics as the transmitted signal.

Both of the above statements are subject to qualification but they have been key assumptions in prior art investigations of the problem.

Prior art approaches to this problem can be divided into two categories. The first is a linear systems approach. In this case, the return signal from a defect is viewed as a convolutional process between the intervening systems (i.e., transducer, medium and defect) and the transmit signal. The second is a phased-array approach in which the return signals from an array of transducers situated in the vicinity of the defect are reconstructed, either in software or hardware, to emphasize its characteristics.

In accordance with the present invention, a model is created relating subsurface fatigue crack size to certain parameters of its reflected ultrasonic signature. The crack size is modeled as a nonlinear combination of these parameters. The type of parameters extracted from these ultrasonic signatures are guided, in large part, from the linear systems theoretic point-of-view. For example, the power spectrum and its associated parameters are selected as inputs to the model because these are key indicators of crack size in the linear system analysis. Furthermore, ultrasonic signatures are obtained by viewing the defect from various transducer positions in the vicinity of the defect, similar to the phased-array approach of prior art investigations. The parameters of these signatures are used to model crack size as a function of the transducer angle.

Ultrasonic signals in the frequency range of 1 to 15 MHz are used because the associated wavelengths are comparable to the crack sizes being investigated. Assuming a shear wave velocity of $1.26 \times 10^8$ mils/second in aluminum, the wavelengths range from 8.4 to 126 mils, and the crack sizes in the sample set are from about 0 to about 279 mils. Therefore, the wavelength-to-defect size ratio is such that the defect acts as an impediment to the waves in the ultrasound beam and a fraction of its energy will be reflected back to the transducer.

The fraction of energy is functionally dependent on the wavelength, the crack geometry, and the properties of the medium. If the defect is "viewed" at any angle other than normal to its plane, interference effects will be manifested in the return signal spectrum. This is so because the reflections from the two edges of the defect will not arrive at the same instant of time and, depending on the crack length, the transducer viewing angle, and the wavelength, the consequent phase relationships between the two reflected waves may lead to a constructive or destructive interference pattern. Furthermore, for any particular crack size and viewing angle, the interference effects will occur at multiple frequencies because of the existence of harmonics of those wavelengths for which phase cancellation or enhancement occurs.

A subsurface fatigue crack is assumed to be planar with grain boundaries no larger than the smallest wavelength in the ultrasonic input signal. The length-to-depth (aspect) ratio of the crack is assumed to be unity. Therefore, a subsurface fatigue crack can be considered a quarter circle planar defect adjacent to the fastener hole bore.

A simplified ultrasonic test procedure comprises a transducer mounted on a plastic wedge atop the material surface. The plastic wedge converts the longitudinal waves, generated by the transducer, into shear waves at the plastic wedge-metal surface interface. The beam is pointed into the material and toward the defect. The method of operation consists of directing an ultrasonic pulse towards the defect. After a certain time interval, the reflected signal is received at the transducer and is available for analysis.

The normal incident position of the transducer is defined to be in a plane perpendicular to the plane of the crack. In this position, the reflected waves from the two edges of the crack — the inner edge toward the fastener hole and the outer edge — arrive in phase at the transducer. This is true for all frequencies because of the normal incident position. Therefore the frequency spectrum of the return signal has essentially the same characteristics as the transmit signal spectrum, except for an amplitude difference. This difference is a function of crack size and material properties. Since the latter is the same for all specimen cracks, the amplitude variations of the return signal should be indicative of crack size.

Apart from collecting return signals from a subsurface defect at the normal incident position, it is desirable to collect data at various other positions by moving the transducer (either mechanically or manually) in the vicinity of the defect. This is motivated by the fact that a component of the planar crack is "visible" to the transducer at different positions — that component is a function of both the crack size and the viewing angle with respect to the normal position. Thus the return signal spectrum, at any position, is a function of crack size and position. Different viewing angles can produce marked changes in the interference effects in the return signal spectrum and they can therefore be useful in characterizing crack sizes.

A set of candidate input parameters is computed for each of the reflected signals from each sample specimen. The parameters are computed from the power spectral and cepstral waveforms — the latter is specifically useful for detecting time-delayed dependent phenomena. An Adaptive Learning Network (ALN) is synthesized from this candidate set. It implements an incomplete 16th order polynomial in the selected input parameters.

Some of the more important parameters selected for automatically modeling purposes consisted of the total power (after certain preprocessing steps) contained in the reflected signal and the cepstral power within specific "quefrency" (i.e., time) bands.

The performance of the resultant ALN model is obtained as follows. If the model output is $\hat{l}$ mils and it is compared to the true value of $l$ mils for each of the two separate recordings of the crack specimens, the model estimated the crack size to within 81.3 percent of the true length for the data in the first series and to within 75 percent for the second series. This is the first known system that is capable of detection and accurate estimation of crack sizes within this range.

The output of the ALN provides a measurement of crack size.

It is therefore an object of this invention to provide a system for location and measurement of subsurface cracks, particularly in the range under 300 mils in length.

It is a further object of this invention to provide an adaptive system for location and measurement of subsurface fatigue cracks.

The above objects and still further objects of the invention will become immediately apparent to those skilled in the art after consideration of the following preferred embodiment thereof, which is provided by way of example and not by way of limitation, wherein.

Figure 4D:
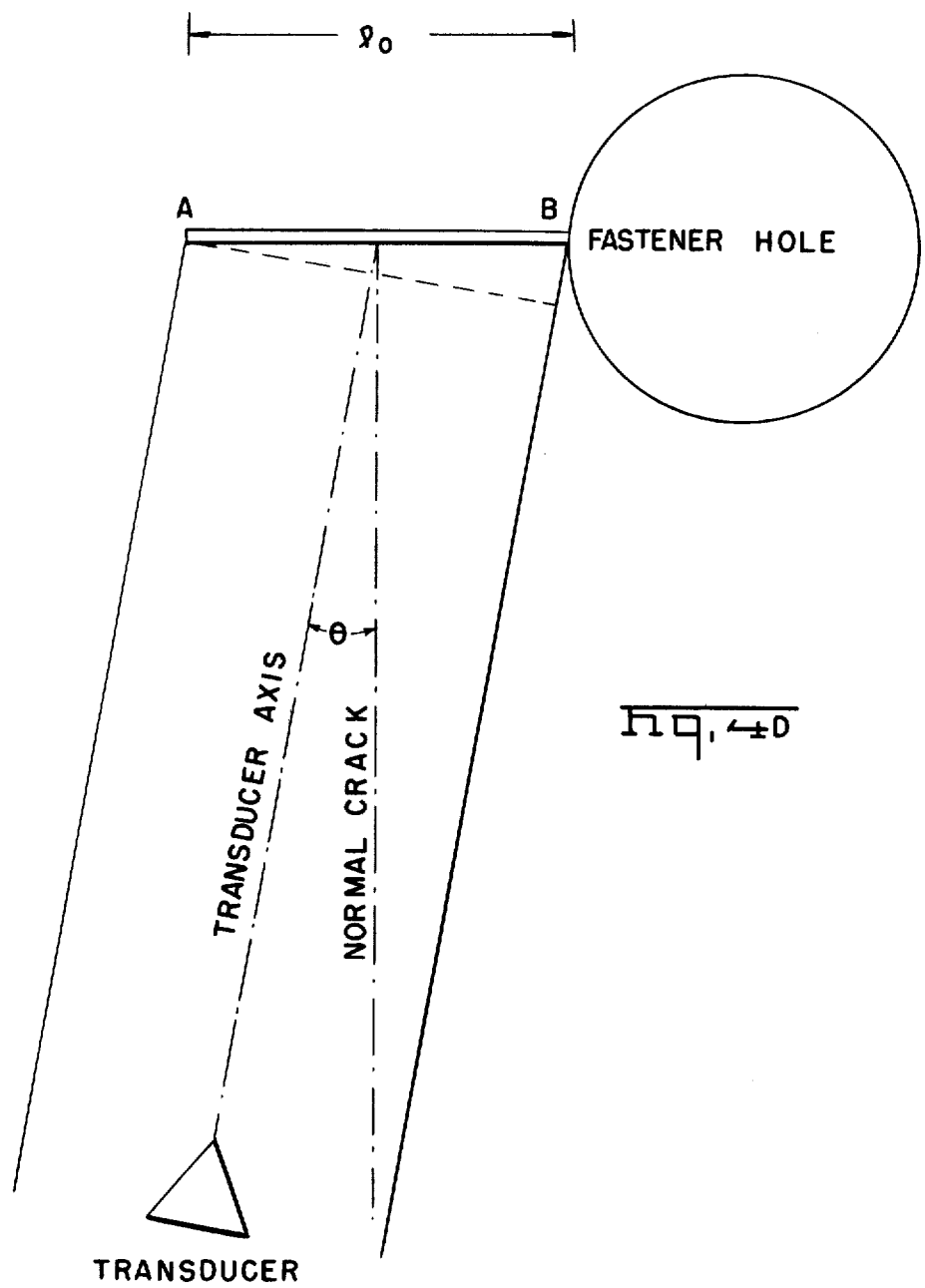
Figure 4E:
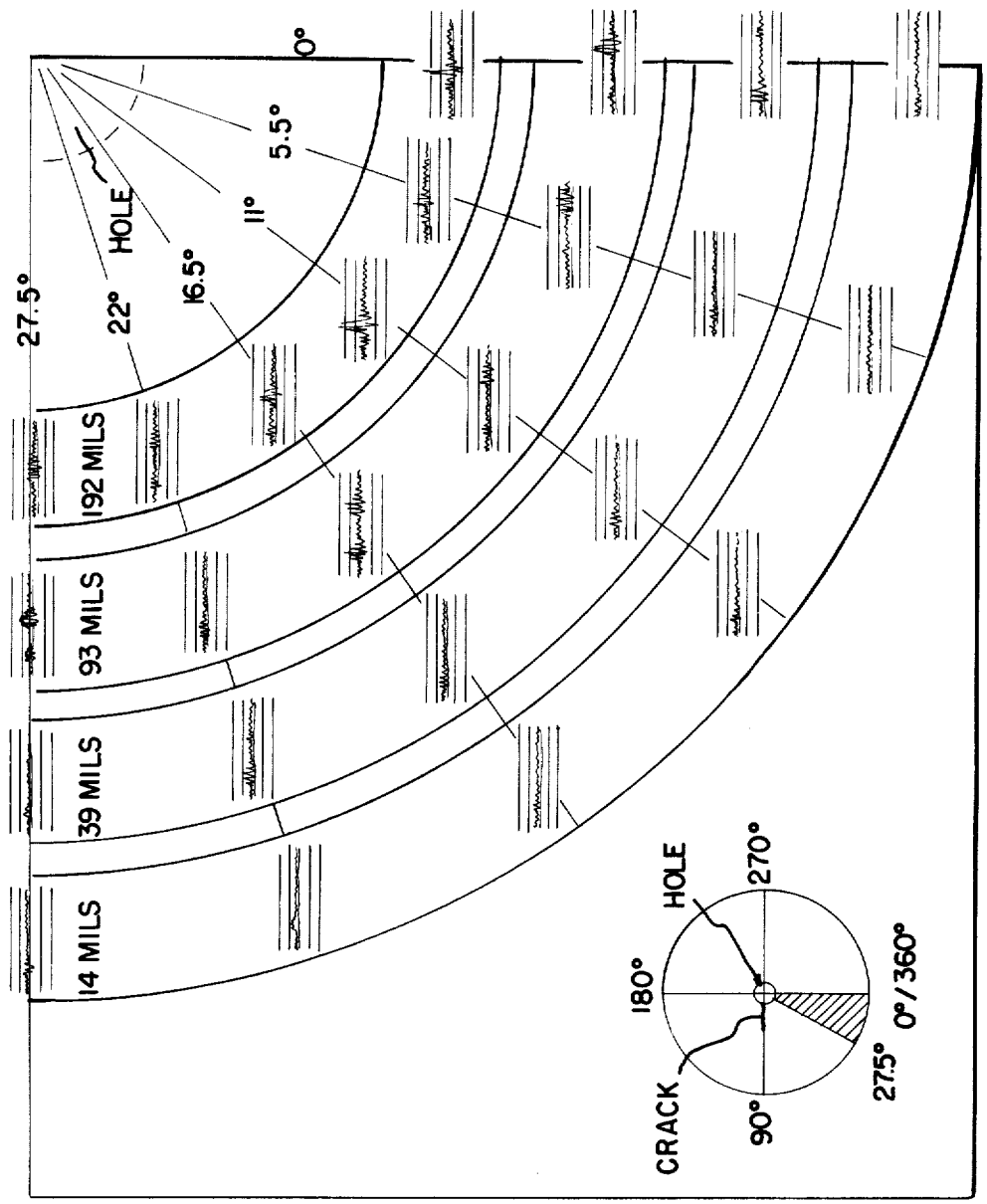
Figure 4F:
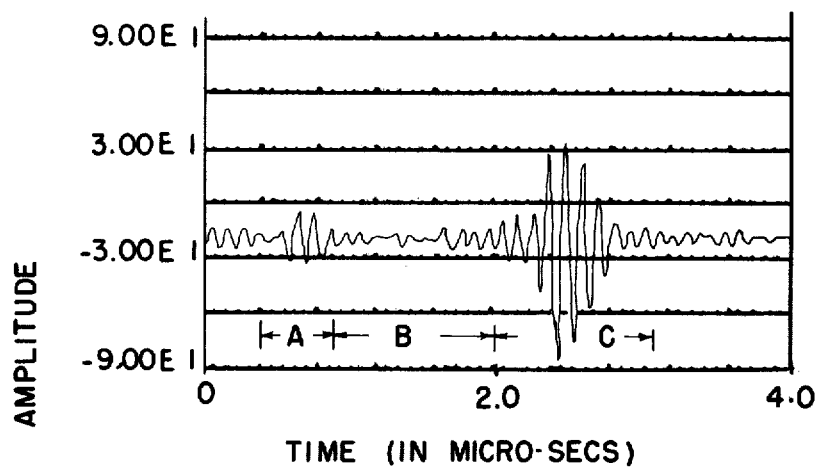
Figure 6B:
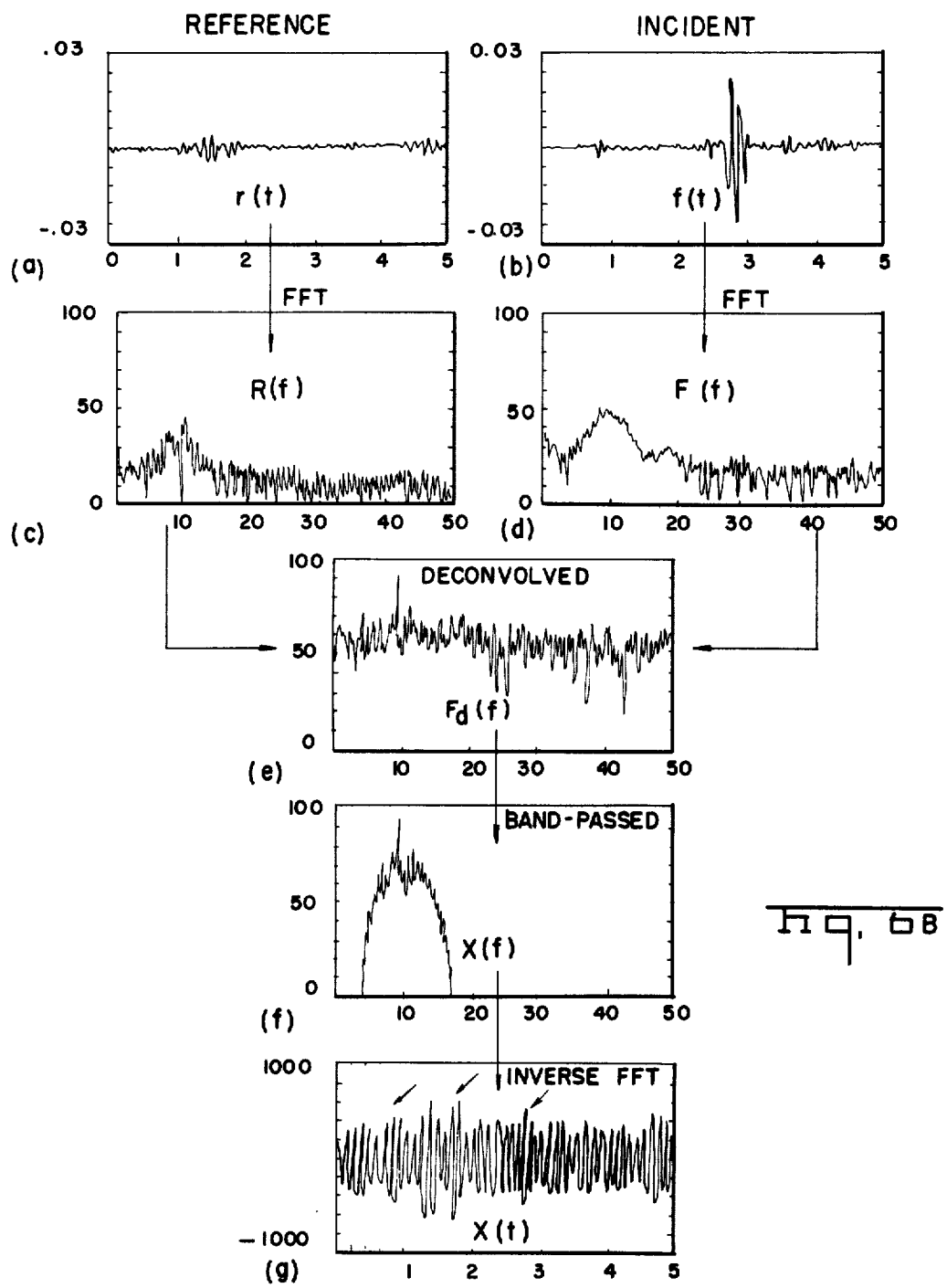
Figure 8:
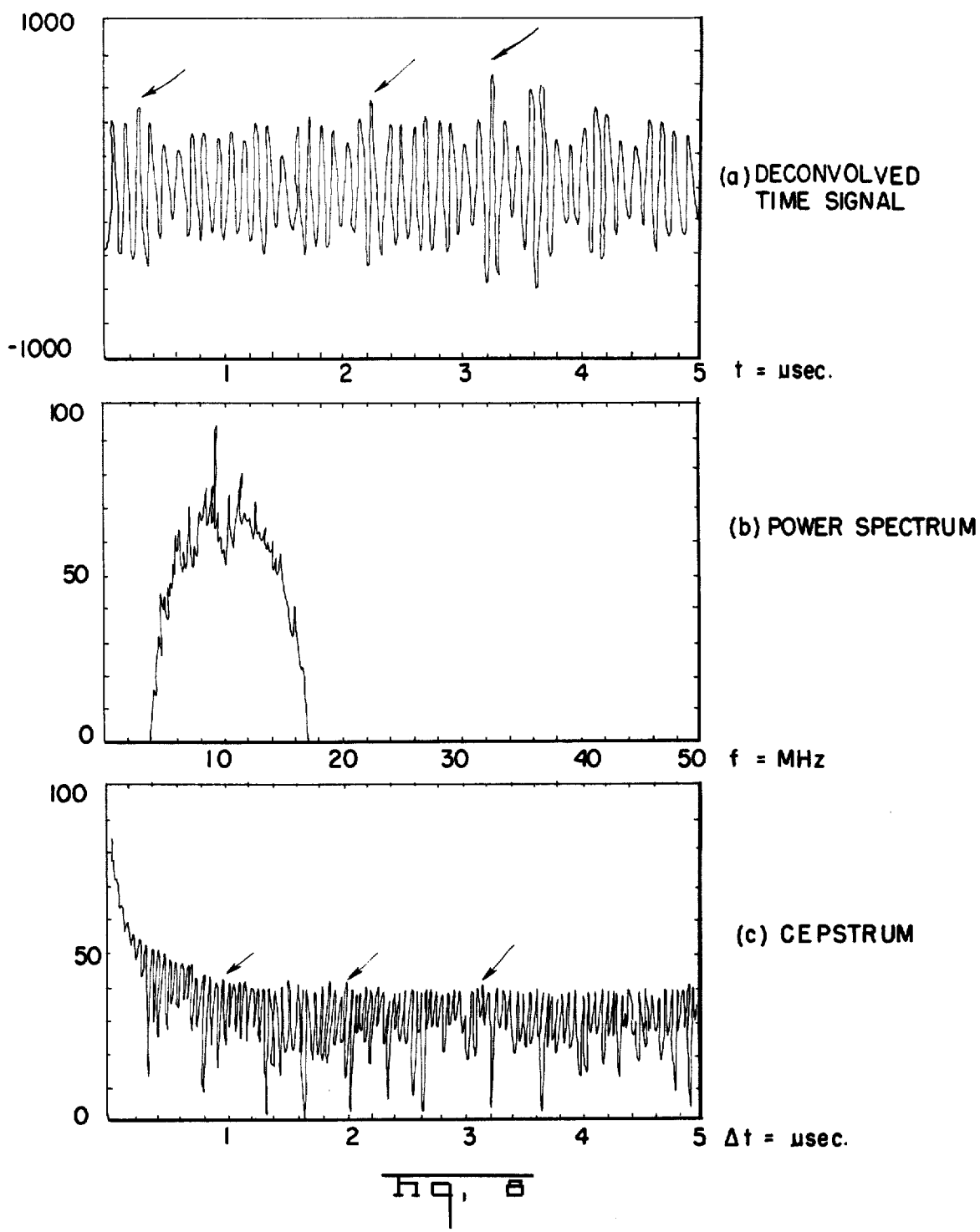
Figure 11B:
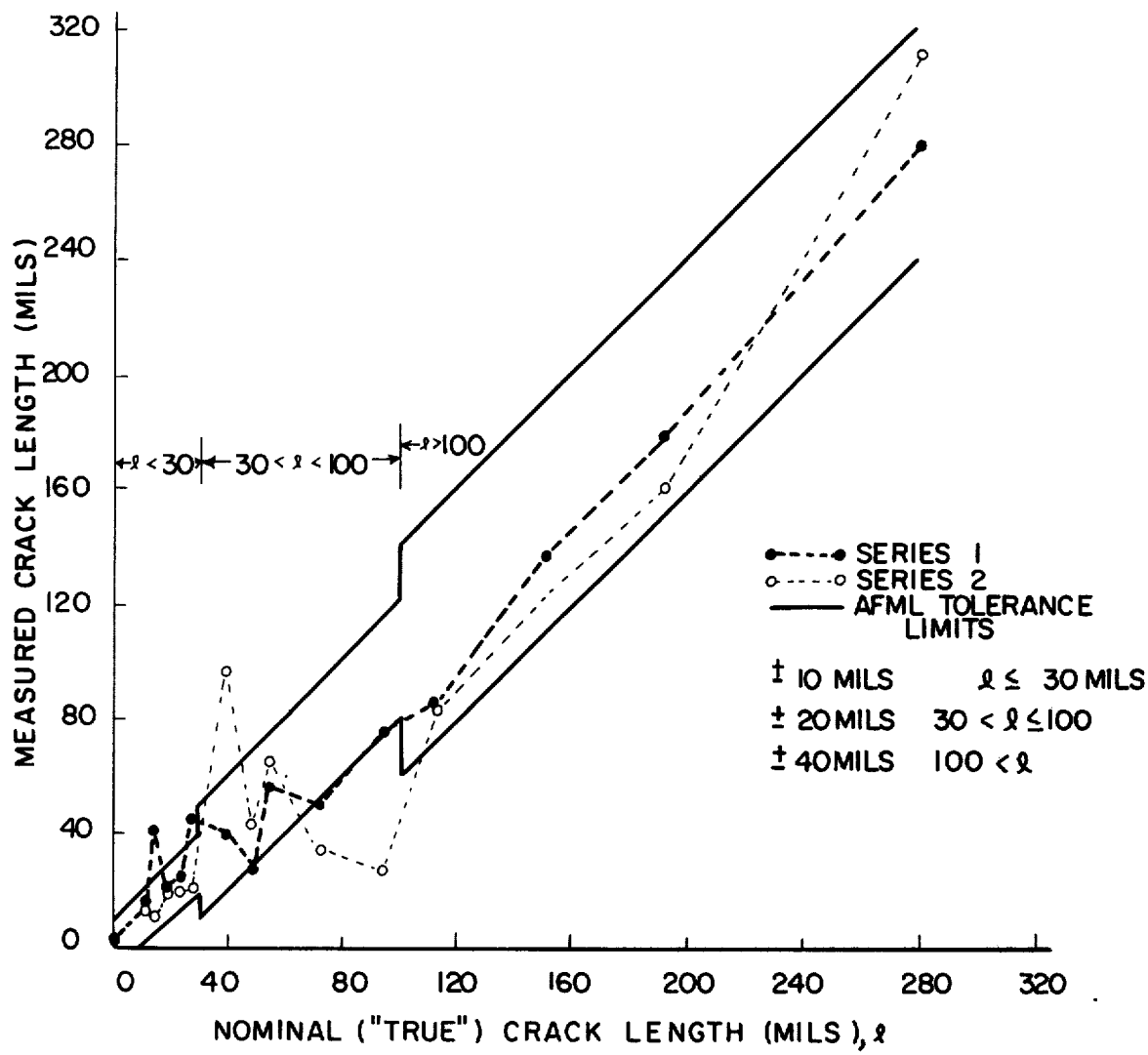
Figure 12:
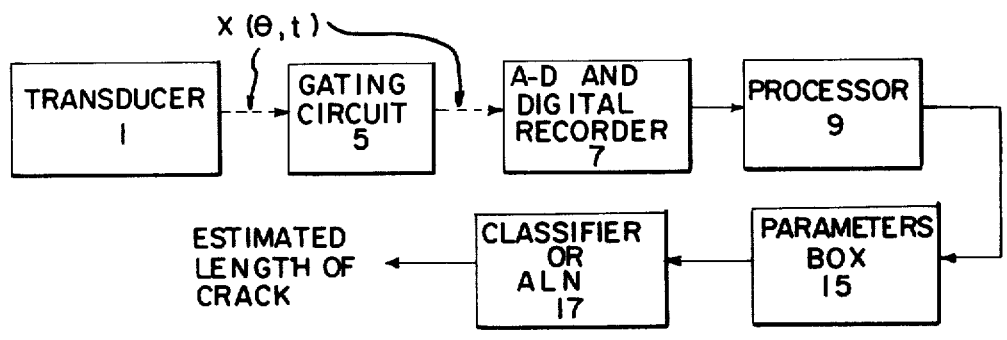
Figure 13:
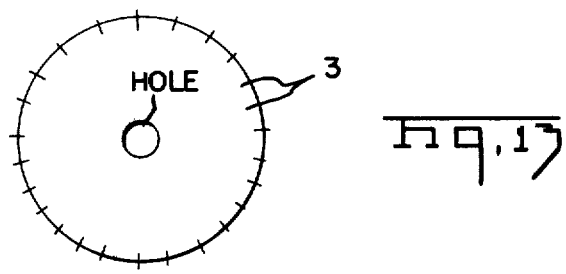

FIGS. 4(a) to 4(c) are a diagram of ultrasonic fatigue crack recoding equipment;

FIG. 4(d) is a diagram of crack reflection geometry;

FIG. 4(e) is a diagram of fatigue crack non-destructive evaluation waveforms recorded from four specimens at six viewing angles;

FIG. 4(f) is a diagram of typical response from a specimen under test viewed at 0° = $\theta$;

FIG. 5 is a diagram of a linear system model of reflection from sub-surface defects;

FIG. 6(a) is a diagram of deconvolution of crack response from a reference signal;

FIG. 6(b) is a diagram of a crack viewed from a reference signal;

FIG. 7 is a diagram of crack response under different transducer conditions;

FIG. 8 is a diagram of waveform processing;

FIG. 9 is a diagram of fatigue crack length signal processing steps;

FIGS. 10(a) and 10(b) show a quantitative surface/sub-surface fatigue crack length measurement system;

FIG. 11(a) is a ALN subsurface fatigue crack measurement model;

FIG. 11(b) is a chart of performance of an ALN quantitative surface/sub-surface fatigue crack length measurement system;

FIG. 12 is a diagram of a complete circuit system in accordance with the present invention;

FIG. 13 is a diagram of a transducer array; and

Figure 14:
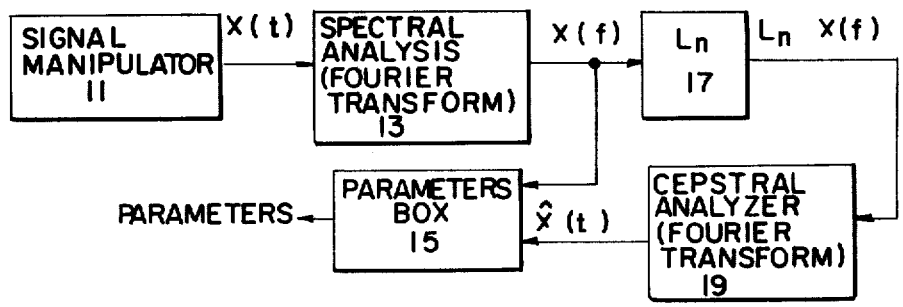

FIG. 14 is a diagram of the processor of the circuit system of FIG. 12.

The circuit in accordance with the present invention is shown schematically in FIG. 12 and includes a transducer mounted around a hole in the metal under test for cracks. The transducer can be a single element which is moved around the hole under test or it can be a series of transducers surrounding the hole at specified distances from each other about a circle as shown in FIG. 13.

The transducers in FIG. 13 are ultrasonic transducers and are capable of producing as well as receiving ultrasonic pulses. The transducer which provides the greatest output is assumed to be normal to a crack and is chosen along with a few additional transducers over a short arc to provide the necessary data, the remaining transducers not being used.

The output of transducer 1 is an analog function of time and angle from the reference transducer (that receiving maximum signal, $x(\theta, t)$ which can be fed to a gating circuit 5 which provides a window by closing before a signal can arrive from the end of the metal under test to eliminate tests wherein no cracks are sensed. This output to an A-D circuit and recorder 7 wherein the analog signal $x(\theta, t)$ is recorded digitally. Alternatively, the gating circuit 5 can be eliminated to remove the window and receive all signals.

The output of recorder 7 is a digital signal and is sent to a processor 9. The processor 9 is shown in greater detail in FIG. 14 wherein the output of recorder 7 is fed to e signal manipulator 11 which is the circuit of FIG. 6(a). The circuit of FIG. 6(a) manipulates the signal to extract the acoustic characteristics of the transducer and medium therefrom since these characteristics are variable from transducer to transducer and from medium to medium of even indifferent areas of the same medium. This is accomplished by using the signals $x(t)$ as the incident signal and obtaining a second signal from a transducer directed away from the hole under test as the reference signal, the reference signal being provided to FIG. 6(a) in digitized form. These time signals are changed from time base to frequency base by undergoing standard Fourier transformation, the frequency signals then being deconvolved to strip them of the acoustic characteristics. The deconvolved signal is filtered to remove frequencies beyond the limits of the transducers. The signal then goes through an inverse Fourier transform to provide the original time signal $x(t)$ wherein the acoustic characteristics of the transducer and medium are eliminated.

The output of the signal manipulator 11 is a function of time $x(t)$ with acoustic characteristics removed, the signal being fed to box 13 for spectral analysis. Box 13 is a spectrum analyzer and takes the Fourier transform of the signal $x(t)$. The output thereof $x(f)$ is fed to a parameters box 15, to be discussed hereinbelow. Also, the natural logarithms is taken in box 17 to provide $Ln\ x(f)$, this being fed to a cepstral analyzer 19 wherein the Fourier transform of $Ln\ x(f)$ is taken. The output of the cepstral analyzer 19 is $\hat{x}(t)$ and is also fed to the parameters box 15.

The parameter box 15, shown in FIG. 9, computes 31 parameters on line $x_4$ to $x_{34}$, the 15 most significant being used herein. These 15 parameters are fed to the ALN 17 or adaptive learning network shown in FIG. 11(a) which computes the estimated crack length from the parameter data received. Each of the boxes in FIG. 11(a) is a bivariate transformation of its two input parameters.

Figure 1:
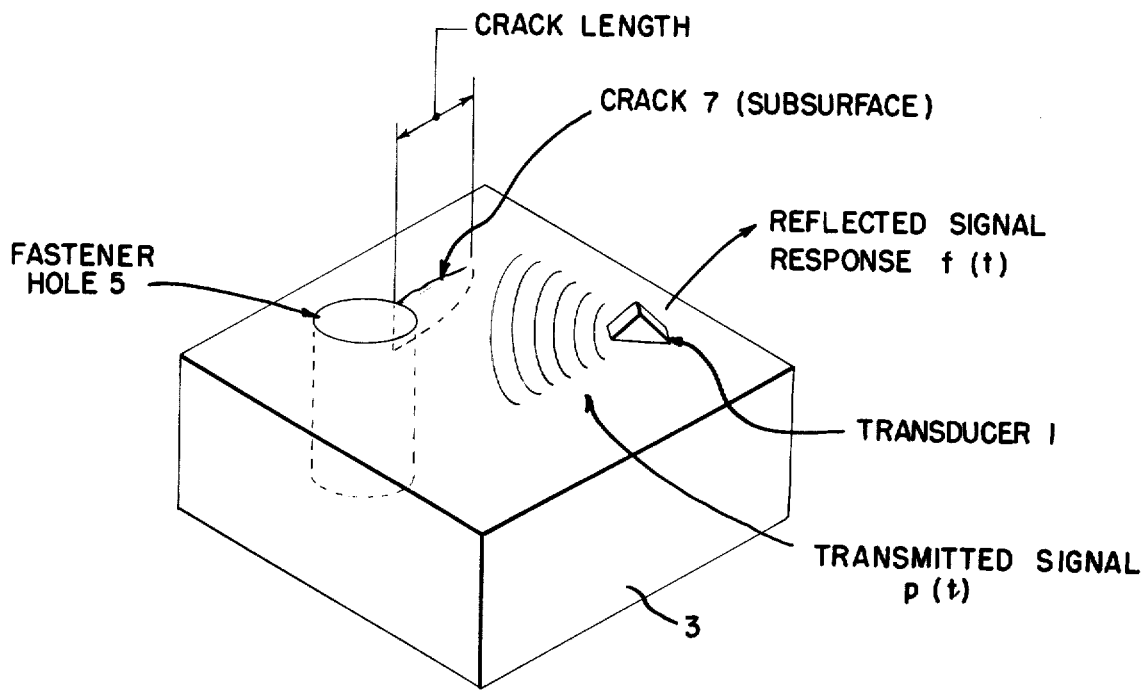
FIG. 1 is a simplified view of an ultrasonic test procedure.

Referring now to FIG. 1, there is shown a simplified ultrasonic testing system. The system includes a transducer for transmitting signals $p(t)$ in the material under Test 3 having a Fastener Hole 5 there through and a Crack 7 to be detected and measured. The transducer also receives the reflected signal response $f(t)$ for transmission to other circuitry to be discussed hereinbelow.

Apart from collecting return signals from a subsurface defect at the normal incident position, it is desirable to collect data at various other positions by moving the transducer (either mechanically or manually) in the vicinity of the defect. This is motivated by the fact that a component of the planar crack is "visible" to the transducer at different positions — that component is a function of both the crack size and the viewing angle with respect to the normal position. Thus the return signal spectrum, at any position, is a function of crack size and position. Different viewing angles can produce marked changes in the interference effects in the return signal spectrum and they can therefore be useful in characterizing crack sizes.

Figure 2:
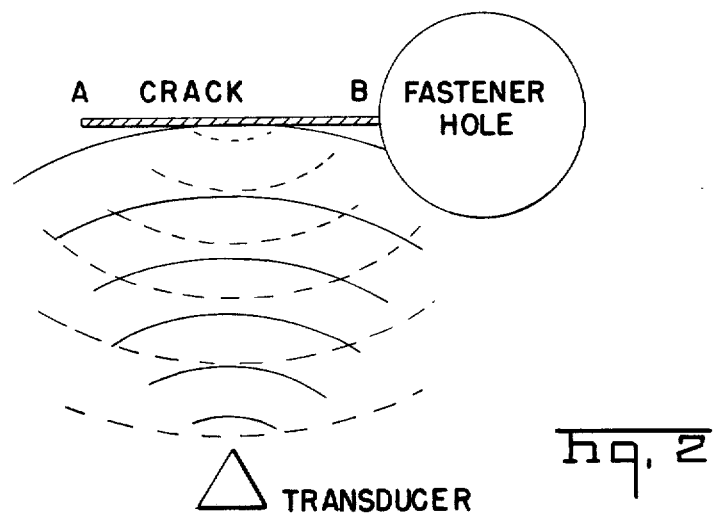
FIG. 2 shows wave patterns with the transducer at the normal incident position.
Figure 3:
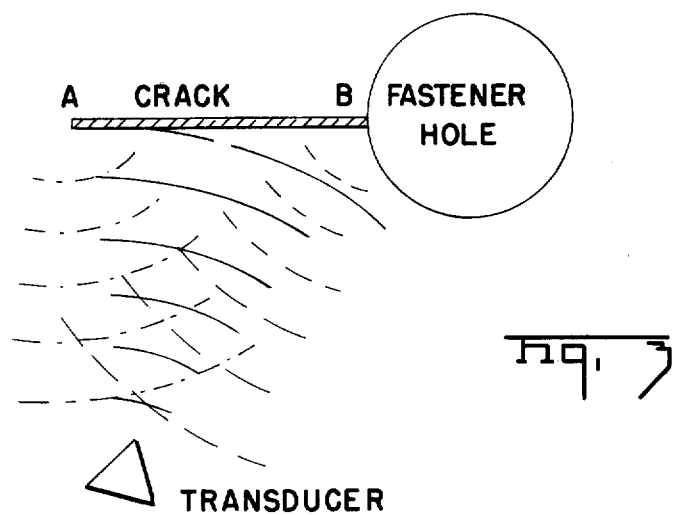
FIG. 3 shows wave patterns with the transducer at an off-normal position.

FIGS. 2 and 3 illustrate why interference effects may be manifested in the return signal spectrum when a defect is viewed at different angles. At the normal incident position (FIG. 2), the transducer's longitudinal axis is perpendicular to the plane of the crack. All waves emanating from the transducer arrive at edges A and B at the same instant of time and are consequently reflected and received in phase at the transducer. Thus the return signal spectrum is essentially the same as the transmit signal spectrum. However, when the crack is viewed at the off-normal position (FIG. 3), the reflection from edge A is received prior to the reflection from edge B. An interference pattern (either constructive or destructive) will be observed in the return signal spectrum depending on the wavelength $\lambda$ of the wave, the differential distance needed for this wave to travel the extra round trip distance to B with respect to edge A, and the viewing angle, $\theta$.

Therefore, a key parameter that determines the amount of constructive or destructive inference at various frequencies and angles is the crack length AB.

A recording system is constructed to scan the hole in a circular manner as shown in FIG. 4(ab), (b) and (c). It includes a transducer positioning device 9 which is free to rotate about the fastener hole. The transducer is attached to the device and can be manipulated to record data at any desired position.

If data recorded at the normal incident position and at five other angular positions in 5.5° increments, in a direction toward the crack, the viewing angle is thereby varied from 0° to 27.5° in 5.5° increments as shown in FIG. 4(c). The transducer is moved to record data at these six positions. The normal incident (0°) position is determined by that transducer viewing angle which elicited the maximum crack response as determined by visual examination of an oscilloscope trace. In addition, a "reference" signal is recorded by pointing the transducer away from the crack. The reference signal contains the hole response alone and is used for deconvolution purposes as described herein below.

FIG. 4(d) is a schematic of the crack reflection geometry. The bold line AB represents the crack and its plane extends into the paper. The extra round trip distance for a wavefront of wavelength $\lambda$, traveling towards corner B with respect to corner A, is $2l_o \sin \theta$. For destructive interference is required.

$$2 l_o \sin \theta = \lambda/2$$

or $$\sin \theta = \lambda/4l_o$$

To observe destructive interference for an 11 mil crack (which is the smallest crack in a sample set):

$$\theta_{mil} = \sin^{-1}\left(\frac{\lambda_{min}}{4l_{min}}\right)$$

$$= \sin^{-1}\left(\frac{4.2}{4 \times 11}\right) = 5.5°$$

Therefore, 5.5° is the smallest angle required to observe a minimum in the power spectrum of a return signal from the smallest crack in the sample set. So, for an 11 mil crack, minima (i.e., "nulls") should occur in the amplitude versus time waveforms at $\theta$ = 5.5°, 16.5° and 27.5°. This result can be used to advantage for an 11 mil crack. Similar reasoning applies for the larger cracks.

FIG. 4(e) illustrates the variety of typical signals obtained from the circular scanning apparatus for the 192 mil, 93 mil, 39 mil, and 14 mil specimens. Each time signal for each crack and viewing angle consists of the reflection from the hole initially, then the response from the inner edge of the crack nearest the hole and, lastly, the response from the outer edge of the crack.

To illustrate the interpretation of each of the plots in FIG. 4(e) a single time plot of a sample viewed at 0° is shown in FIG. 4(f). The time window is 4 microseconds. The signal during time interval marked "A", which is approximately 0.5 microseconds in duration, is the response from the outer surface of the fastener hole. The signal during time interval marked "C" is the reflection from the outer and inner edge of the crack. Interval "B" is the time between these two events.

Each plot in FIG. 4(e) contains the three time intervals described above, although the duration of each is functionally dependent on the crack length and the viewing angle. The sequence of occurrence of the event is always the same as in FIG. 4(f) i.e., the hole response followed by a crack response. As explained above, this is so because the fastener hole is closest to the transducer and its reflection is received initially. Also, as the viewing angle increases, the response from the outer and inner edges of the crack tend to "creep up" on one another because the difference in their physical distances from the transducer decreases. The hole response, however, always occurs at the same instant of time. The time of occurrence of the hole response is used as a reference time for gating the crack response in the data window, because the time of occurrence of the latter varies with crack size and viewing angle, whereas the former is fixed.

Examining FIG. 4e one can observe the interference phenomenon being manifest. For example, a 192 mil crack has a large response at the 0° position, decreases somewhat at 5.5°, and increases again at 11°. Large responses are elicited from the 93 mil crack at 0° and 16.5°; the preferred viewing angles for a 39 mil crack are 0° and 22°.

The smaller cracks — 39 and especially 14 mils in the figure — have barely discernible responses and are difficult, if not impossible, to distinguish from the background noise (in spite of the fact that signal averaging was performed to minimize equipment noise. The information relative to the cracks is, of course, resident in their reflected signals, even though it may not be apparent from visual examination of the amplitude versus time traces.

For each viewing angle $\theta$, the data window for analysis included both the response from the outer surface of the fastener hole and the response from the crack, because the time of occurrence of the former is predictable, whereas the time of occurrence of the latter varies with both the crack geometry and the viewing angle. The data window was sufficiently long to include the crack response, but not spurious reflections from other sources or multipath reflections.

In summary, the approach to data collection for the crack detection procedure is an integration of both the "linear systems" and the "phased-array" approaches. The reflection of ultrasonic signals from a subsurface defect is considered as an output from a "black box". The constituents of the black box are the medium, the transducer, and the defect, but the analytical relationship among them is unknown. The problem lies in extracting the characteristics of the defect from the output of the black box. Linear signal processing techniques alone are not capable of resolving defect size. Therefore, the best one can do under the circumstances of lack of knowledge concerning the underlying analytical relationships is to construct an empirical mathematical model based on known parameters of the output response and the intrinsic nature of the defect.

A mathematical description of the reflection of ultrasonic signals from subsurface fatigue cracks and equations relating the crack size to parameters of the input is now provided.

Three waveforms— power spectrum, cepstrum, and spatial transform— are computed from the recorded amplitude versus time waveforms.

The recorded pulse echo $f(t)$ of the return signal is composed of the contributions from a number of systems as shown in FIG. 5 If all the intervening systems (i.e., the transducer, the medium and the crack) are modeled as linear systems and the return echo is a convolutional process, the return signal is written as, $$f(t) = p(t) h(t) * m(t) * g_l(t) * m(t) \& h(t) \qquad (6.1)$$

where the asterisk denotes the convolution operator. Equation 6.1 can be conveniently written in the frequency domain as $$F(f) = P(f) H^2(f) M^2(f) G_l(f) \qquad (6.2)$$

where the upper case letters indicate (Fourier) frequency transforms of the individual systems.

If the pulser emits a perfect impulse and the transducer is sufficiently broadband to pass all the frequencies of the pulser, and if the medium characteristics do not change from one subsurface crack to another, the return pulse echo from any crack is $$F(f) = M^2(f) G_l(f) \qquad (6.3)$$

where $M(f)$ is the frequency response of the medium and $G_l(f)$ is the frequency response of the crack (of length $l$).

In other words, the return echo can be modeled validly as a linear function of the crack response if these assumptions are true.

Since the cracks are area-amplitude reflectors, the larger size cracks produce larger reflections. Furthermore, all frequencies incident to the plane of the crack are reflected and received in phase at the transducer. Therefore, the return echo is solely dependent on the size of the crack.

The above assumptions of the characteristics of the transducer and the medium are too stringent to be realistic. The typical frequency response of a 10 MHz transducer would cover a bandwidth of approximately 8 MHz. Moreover, the frequency response of transducers change even though they may be identically rated. The medium characteristics may also change depending on the structural and the metallurgical properties of a local region. Hence, for either or both reasons, the response (Equation 6.2) will change for the same crack under different test conditions. On the other hand, one would desire the response of a particular size crack to be invariant, or at least relatively insensitive, to different operating conditions. A signal preprocessing procedure is provided to cope with these transducer and medium variabilities. It is derived as follows.

An inverse filtering operation can be performed to minimize the effects of the transducer and the medium. A reference signal can be recorded (similar to the scheme shown in FIG. 5) by replacing the crack by a point source defect which has an all-pass characteristic. Therefore, $R(f)$ is recorded which is, from Equation 6.2, $$R_p(f) = P(f) H^2(f) M^2(f) \qquad (6.4)$$

The point source defect has unity response at all frequencies, and hence $G_l(f)$ does not appear explicitly herein below. Deconvolving Equation 6.4 from Equation 6.2, which is division in the frequency domain, gives $$F_d(f) = \frac{F(f)}{R_p(f)} = G_l(f) \qquad (6.5)$$

That is, the recorded deconvolved signal is characteristic solely of the crack.

If the reference signal is not obtained from a point source defect but from a standard size crack, $R_s(f)$ can be modeled as $$R_s(f) = P(f) H^2(f) M^2(f) G_s(f) \qquad (6.6)$$

where $G_s(f)$ is the frequency response of the standard size defect.

Deconvolving Equation 6.6 from Equation 6.2:

$$F_d(f) = \frac{F_s(f)}{R_s(f)} = \frac{G_c(f)}{G_s(F)} \quad (6.7)$$

where the deconvolved signal, although stripped of medium and transducer effects, still has the standard size defect characteristics imbedded within it.

The crack characteristics can still be exclusively extracted by homomorphic filtering procedures which convert a nonlinear operation such as multiplication or division into one of addition or subtraction. Specifically, the logarithm of both sides of Equation 6.7 is taken:

$$\log\{F_d(f)\} = \log\{G_c(f)\} - \log\{G_s(f)\} \quad (6.8)$$

and Equation 6.8 is rewritten as $$F_d'(f) = G_c'(f) - G_s'(f) \quad (6.9)$$

where the primes indicate the log of the frequency transforms.

By the principle of superposition, the inverse transform of Equation 6.9 is $$f_d'(t) = g_c'(t) - g_s'(t) \quad (6.10)$$

and the deconvolved signal in the time domain $f_d'(t)$ is a linear algebraic combination of the crack response and a standard size defect which does not vary from one crack to another. The signal $f_d'(t)$ is called the cepstrum of $F_d(f)$. In other words, the cepstral transform converts a nonlinear operation in the frequency domain (Equation 6.7) to a linear operation in the time domain (Equation 6.10).

Therefore, in summary, an ultrasonic signal from a subsurface defect can be modeled approximately as a linear system (under given assumptions) which consists of the transducer, medium, and the defect characteristics. To analyze the crack characteristics, one resorts to an inverse filtering operation to strip the medium and transducer effects from the output signal. In the case where a reference signal is not recorded from a point source defect, an inverse filtering operation can still be carried out by homomorphic techniques, which reduce a nonlinear operation such as multiplication of waveforms to a linear operation.

The six circularly scanned signals and the reference signal, described hereinabove in FIG. 4, comprises a set of seven readings for a particular crack. Each of the six scanned signals consisted of 20.48 microseconds of data, sampled at 10 nanoseconds per point. The physical distance between the outer rim of the fastener hole and the transducer is known exactly, so the time of arrival of the reflection from it was estimated accurately. The arrival time did not change with changes in the viewing angle or in crack size because the distance between the transducer and the fastener hole was fixed.

However, as explained above, the arrival time of the crack reflection changes with both viewing angle and crack size. As the viewing angle increases, the crack response tends to "creep up" on the hole response. If the crack size is smaller, the time duration of the crack response is lessened. Therefore, for either or both reasons, the time of arrival of the crack response could not be accurately estimated. It was thereby decided to use both the hole and crack response for analysis. A 512-point window, containing the two responses, was isolated from the 2,048-point sampled signal for each of the six circularly scanned signals per specimen. The time axis location of the data window is established via visual examination of the data base.

The data window for the seventh, or reference signal, in each set of readings is recorded in the same way as the other six signals. The transducer is positioned away from the crack region of the hole. This signal consists of the hole response alone and it occurs at the same instant that the hole response is observed in the circularly scanned signals. The reference signal is thus a function of the characteristics of the medium, the transducer, and a standard sized defect—the fastener hole in this case. From the theoretical development, the reference signal can be used, in principle, to deconvolve the six circularly scanned signals in order to minimize medium and transducer effects. Unfortunately, because all transducers are band-limited, Equation 6.7 cannot be fully realized. In practice, the only true frequencies in the deconvolved signal are resident in a limited band. If the transducer is rated for 10 MHz with 3db cut-off frequencies at 6 and 14 MHz, the data collected for the reference and the crack signal are also band-limited. Furthermore, the process of deconvolution introduces spurious frequencies beyond the 3db range of the transducer (due to dividing small numbers by other small numbers) and these have to be suppressed. The spurious frequencies are suppressed by filtering the deconvolved signal through a gaussian band-pass filter, which has a sharp cut-off at the 3db frequencies. The advantage of using the gaussian filter rather than the standard box filter is that, in the time domain, the tail of the former has fewer side lobes than does the latter.

FIG. 6(a) outlines the sequence of operations to obtain the deconvolved signal for each of the six angular positions of the transducer. FIG. 6(b) shows the resultant signals obtained, at each step in FIG. 6(a), for a 279 mil crack viewed normal to the plane of the crack. The signal obtained after deconvolution (FIG. 6(b)(e)) has an all-pass characteristic in the frequency domain with the relevant information contained in the 6–14 MHz band (FIG. 6(b)(f)). After bandpass filtering, the deconvolved time waveform is plotted (FIG. 6(b)(g)) and, not surprisingly, the most prevalent frequencies are between 6–14 MHz, with a predominance around 10 MHz.

If the transducer were indeed not band-limited, the deconvolved time signal would have an impulse at about the instant when the hole response is observed and another set of impulses where the crack begins and terminates. The time between the latter two impulses is indicative of the length of the crack relative to the viewing angle of the transducer. However, because the transducer is band-limited, its convolution with the impulses produces the "ringing" effect as shown. The approximate positions of the impulses are indicated by arrows in FIG. 6(b)(g).

Although deconvolution is helpful in minimizing transducer and medium effects, the bandwidth limitation of the transducer is inescapable. The deconvolved time signal still contains some global transducer characteristics such as the center frequency of 10 MHz, so a different transducer with a different rating (say 5 MHz), would result in a different resultant signal. However, the variations of different 10 MHz transducer frequency spectra have been minimized. Consequently, after a given center frequency transducer family has been chosen, such as 10 MHz, the deconvolution process is helpful in minimizing the effects of the external medium and transducer variations.

It is also observed that the peaks in the deconvolved time signal is indicative of the length of the crack for a certain transducer viewing angle. However, because of the bandwidth of the transducer, the peaks are "smudged" and a ringing effect is produced as shown in FIG. 6(b).

It is desirable to minimize the characteristics of the bandpass filter and also to emphasize the peaks in the deconvolved time signal. To accomplish this, a cepstral analysis is performed on the deconvolved time signal.

The cepstrum is defined as the inverse Fourier transform of the logarithm of the power spectrum. Referring to FIG. 6(b), the bandpassed, deconvolved power spectrum $X(f)$ is $$X(f) = F_d(f)B(f) \tag{6.11}$$

where $F_d(f)$ is the deconvolved power spectrum of the crank signal, and $B(f)$ is the spectrum of the bandpass filter. Taking the log of Equation 6.11 (as was done for Equation 6.8) reduces it to an additive process, i.e., $$\log\{X(f)\} = \log\{F_d(f)\} + \log\{B(f)\} \tag{6.12}$$

or $$= F_d'(f) + B'(f) \tag{6.13}$$

where the primes indicate the log transform of the respective frequency response.

By taking the inverse Fourier transform of the left hand side of Equation 6.13, and using the principle of superposition, the time response is $$x'(t) = f_d'(t) + b'(t) \tag{6.14}$$

where the lower case letters are the individual inverse Fourier transforms. In other words, the cepstrum of $X(f)$ is a sum of the cepstra of $F_d(f)$, which is a characteristic of the crack and the viewing angle, and of $B(f)$, which is a characteristic of the bandpass filter, and does not change from one experiment to another.

The signal $f_d(t)$ is not used alone because it is noise prone beyond the 3 db frequencies of the transducer. The filter response $b'(t)$ has the effect of suppressing these frequencies and still retain the linear relationship between the resultant signal, $x'(t)$, and the deconvolved signal, $f_d'(t)$.

Therefore the cepstral signal $f_d'(t)$ bears important information about the crack length and the viewing angle.

The crack response signal is composed of the response from the hole and the crack. Ideally, it should consist of three impulses as shown in FIG. 7(a), where $t_h$, $t_b$, and $t_e$ indicate the instant of occurrence of the reflection from the hole, the beginning of the crack and the end of the crack, respectively. The time $t_h$ is independent of the size of the crack, whereas $t_b$ and $t_e$ change with transducer viewing angle and crack size.

The crack response to the band-limited signal would resemble FIG. 7(b), and has the effect of "smudging" the impulses. The narrower the bandwidth of the transducer, the broader the smudging. Nevertheless, the same phenomenon is manifest at $t_h$, $t_b$, and $t_e$. After computing the cepstrum of the response of FIG. 7(b), peaks are manifest clearly at instant $t_b-t_h$, $t_e-t_b$ and $t_e-t_h$ as shown in FIG. 7(c), and they are functions of crack length and viewing angle. As the transducer viewing angle is varied, $t_b$ begins to creep up on $t_h$, which remains fixed, and $t_e$ remains approximately the same. If the crack size were different, $t_b$ and $t_e$ would be different; for smaller cracks $t_b$ and $t_e$ would decrease.

Therefore, the positions of the peaks in the cepstrum are indicative of the size of the crack and the viewing angle of the transducer. Since the viewing angle is known, the crack size is thus inferable.

Unfortunately, in the actual physical environment, the resolution of the cepstral peaks is not very clear due to three main factors:

1. The system is not linear.
2. There are multipath reflections which have not been treated in the analysis.
3. The limited bandwidth of the transducer has the effect of smudging the peaks in the deconvolved time signal.

FIG. 8(a) shows the deconvolved time signal for a 279 mil crack viewed at 0°. The corresponding power spectrum and the cepstrum are shown in FIGS. 8(b) and 8(c). The most probable location of $t_h$, $t_b$, and $t_e$ are 0.25, 2.25, and 3.25 microseconds respectively, and are shown as arrows in FIG. 8(a). The impulses, as should be expected, are really sampling functions (sin $x/x$) because of the finite bandwidth of the transducer. The cepstrum should reveal peaks around the various time differences $t_e-t_b$, $t_b-t_h$ and $t_e-t_h$, i.e., 1, 2, and 3 microseconds. At the corresponding points in the cepstrum, local maxima can be observed (arrows) in FIG. 8(c). However, the peaks are not clearly resolved, and once again, a statistical procedure of counting the peaks in certain bands of the cepstrum must be employed.

The deconvolved crack response discussed above is helpful in analyzing the characteristics of the crack, stripped of medium and transducer characteristics. However, for a particular crack, its response will change with different viewing angles of the transducer. In other words, a family of crack responses in time is available—each member of the family corresponding to a particular viewing angle. Thus the crack response is sampled both in time (512 points at 10 nanoseconds/point) and space (six viewing angles from 0° to 27.5°, in 5.5° increments). Time and space represent two independent bases of evaluation of the crack characteristics. As explained above, there are changes in the time response due to changes in the viewing angle (i.e., interference effects). The question is how can one best unify the variations in time and space to deduce a global description of the characteristics of the crack?

The following analysis shows that a spatial transform can be defined to describe crack characteristics in time as well as space. Its practical use and limitations are also discussed.

Consider a planar crack of length $l_o$ which is ultrasonically illuminated by a transducer a fixed distance from the center of the fastener hole (FIG. 4(d)). The main wavefront emanating from the transducer is at an angle $\theta$ with respect to the normal to the crack plane.

The excess distance needed for an ultrasonic wave of wavelength $\lambda$ to travel to B relative to A, is $2l_o\sin\theta$, and the phase shift at the transducer relative to a frequency $f$ is $$\phi(f,l_o,\theta) = \frac{4\pi l_o \sin\theta}{\lambda} = \frac{(4\pi l_o \sin\theta)f}{c} \quad (6.15)$$

where $c$ is the ultrasonic shear wave velocity in the material.

If the transducer has an impulse response $A(f)\exp(j\gamma_f)$ at frequency $f$, the return signal from the crack can be described as $$R(f) = k\, A(f)\exp\{j(\gamma_f + \phi(f,l_o,\theta))\} \quad (6.16)$$

wherein $k$, a fraction, is the reflectance coefficient and it is a property of the material; and $\phi(f,l_o,\theta)$ is defined in Equation 6.15. Dividing Equation 6.16 by the impulse response of the transducer, the deconvolved response is obtained as $$D(f) = k\, \exp\{j\phi(f,l_o,\theta)\} \quad (6.17)$$

A spatial variable, $\Omega$, can be defined as:

$$\Omega = \frac{4\pi f \sin\theta}{c} \quad (6.18)$$

which has units of $1/l$. Therefore, Equation 6.17 becomes $$D(\Omega) = k\, \exp(j\Omega l_o) \quad (6.19)$$

If the transducer has frequencies, $f$, extending from 0 to $\infty$, then $\Omega$ has the same range (from Equation 6.18) and $D(\Omega)$ is defined as in Equation 6.19 but with $$D(\Omega) = k\, \exp(j\Omega l_o),\ 0 < \Omega < \infty, \quad (6.20)$$

which is a sinusoidal function of $\Omega$ with frequency $l_o$.

The inverse Fourier transform of $D(\Omega)$, defined as $S(l)$, is:

$$S(l) = \int_0^\infty D(\Omega)\exp(-j\Omega l)d\Omega,\ (0 < l < \infty) \quad (6.21)$$

$$= k \int_0^\infty \exp(j\Omega l_o)\exp(-j\Omega l)d\Omega \quad (6.22)$$

$$= k\, \delta(l - l_o) \quad (6.23)$$

which is an impulse of height $k$, at $l = l_o$ in the $l$-space. Therefore, in theory, the complex frequency spectrum at any particular viewing angle can be deconvolved from the complex frequency spectrum at 0° viewing angle and, by any appropriate transformation into the $\Omega$ space, the deconvolved spectrum in the $\Omega$-space can be inverse transformed to reveal an impulse in the $l$-space at $l_o$, the crack length.

The function $S(l)$ is defined to be the spatial transform and it consists of an impulse at $l_o$ in the $l$-space. Notice that $\Omega$ can be varied by either changing the frequency $f$ or the angle $\theta$, or both. Hence, the term "spatial transform" to denote the function S.

The fatigue crack experimental apparatus comprises collecting the reflected time signal from a crack at six viewing angles, including the normal position ($\theta = 0°$) The complex Fourier transform at each viewing angle is band-limited both in the frequency $f$, because of the transducer limitations, and consequently in the spatial frequency, $\Omega$ (Equation 6.18).

One can still compute a band-limited spatial transform $S(l)$ but, unfortunately, even though the frequency sampling $f$ is equally spaced, the sampling in the $\Omega$-space is uneven because of the non-linear transformation of frequency $f$ and of angle $\theta$ in Equation 6.18. However, a family of spatial transforms can still be derived for each viewing angle $\theta$—each one having a bandwidth in the $\Omega$-space which is a function of: (1) the viewing angle, and (2) the frequency bandwidth of the transducer.

Because of the finite sampling interval in the time domain (10 nano-seconds) and because of the finite length of the complex transform in the $f$-domain, the sampling interval $d\Omega(\theta)$ in the $\Omega$-space is finite:

$$d\Omega(\theta) = \frac{4\pi \sin\theta}{c} df \quad (6.24)$$

and it increases with $\theta$. Consequently, by the Nyquist criteria, the largest crack which can be detected by the spatial transform $S(l)$ in the $l$-space, varies inversely with $\theta$; the larger the viewing angle $\theta$, the smaller the maximum crack length that can be detected.

Table 1 hereinbelow shows the maximum and minimum values in the $\Omega$-space and the corresponding maximum and minimun valves in the $l$-space for the six viewing angles. The frequency bandwidth of the transducer lies between 6–14 MHz; the sampling interval is 10 nanoseconds in the time domain with a frequency resolution of 0.195 MHz. The velocity of ultrasonic shear wave in aluminum is 3200 meters/second. The lowest and highest spatial frequencies, $\Omega_l$ and $\Omega_h$, in columns 3 and 4 are computed by substituting the lowest and highest frequencies, $f_l$ and $f_h$, in Equation 6.18.

The $\theta = 0°$ position is used as the deconvolution signal as per Equation 6.17 because the relative phase shift $\phi(f,l,0)$ is zero at all frequencies.

TABLE 1

MAXIMUM AND MINIMUM SPATIAL FREQUENCIES AND THE MAXIMUM AND MINIMUM CRACK LENGTHS WHICH CAN BE RESOLVED AT EACH VIEWING ANGLE

| Angle | | Spatial Frequency | | Spatial Sampling Rate | Crack Length Resolution (Mils) | |
|---|---|---|---|---|---|---|
| $\theta$ | Sin $\theta$ | Lowest ($\Omega_l$) | Highest ($\Omega_h$) | $d\Omega$ | Lowest $1/\Omega_h$-$\Omega_l$ | Highest $1/2d\Omega$ |
| 0 | 0 | 0 | 0 | INDETERMINATE | | |
| 5.5 | 0.0958 | 0.0574 | 0.1338 | 0.0019 | 13.075 | 268.0 |
| 11° | 0.1908 | 0.1142 | 0.2665 | 0.0039 | 6.6 | 134.7 |
| 16.5 | 0.2840 | 0.1700 | 0.3966 | 0.0055 | 4.41 | 90.5 |
| 22.0 | 0.3746 | 0.2242 | 0.5231 | 0.0073 | 3.3 | 68.6 |
| 27.5 | 0.4617 | 0.2763 | 0.6448 | 0.0090 | 2.7 | 55.6 |

It is clear from Table 6.1 that the largest crack which can be resolved is 268 mils when the transducer is at the 5.5° position. The maximum detectable crack progressively becomes smaller as the transducer is moved from 0° to 27.5°. At 27.5°, the largest crack which can be resolved is 55.6 mils. Therefore, many of the larger cracks (279 mils, 192 mils, etc.) are too infrequently sampled in the Ω-space to be detected in the *l*-space.

However, one can imagine the inverse problem—knowing the location of the impulse in the *l*-space (i.e., the size of the crack), can it be predicted where the impulse will occur if it is insufficiently sampled in the Ω-space? The answer is yes, because an aliased version of the impulse will appear in the low frequency range of the *l*-space, and its location can be computed exactly from the Nyquist sampling theorem. In fact, the crack can be as large as possible, and it will still appear in the limited range of S(*l*)—only the number of "fold-overs" has to be computed to determine its exact location in the *l*-space.

There are four main reasons why the spatial transform S(*l*) (Equation 6.23) in the *l*-space will not be an impulse:
1. The fatigue crack is not a perfect reflector and multipath reflections cannot be precluded.
2. The deconvolution step (Equation 6.7) is a noise-inducing process.
3. The 0° viewing angle is used to deconvolve the other five signals in the deconvolution step (Equation 6.17); all frequencies might not be reflected in phase for the 0° signal.
4. In the discrete *l*-space an impulse function is manifest as a sampling function (sin $x/x$ type); the aliasing of a function other than an impulse is more complicated.

For all of these reasons, an impulse distribution will be obtained rather than a single impulse in the *l*-space for each fatigue crack. Therefore, a statistic of the spatial transform curve is computed. The closest statistical approximation to the location of an impulse is the expected value of the spatial transform curve.

Therefore, to use this technique, one constructs the spatial transform as in Equation 6.21, but in the discrete domain. A course estimate of the true-crack length is needed to determine if the spatial transform S(*l*) curve contains aliased frequencies in the *l*-space. The estimate is further used to compute the number of fold-overs of the spatial transform curve, and then its expected value is computed to be an estimate of the crack length.

The spatial transform technique is a means by which both the time variation in the reflected signal and the transducer viewing angle can be unified in a spatial transform to reveal an impulse in the spatial domain such that its location in the *l*-space corresponds to the crack length (Equation 6.21).

Based on the above presentation, the following parameters were computed as candidate inputs to the ALN model.

The parameters extracted from the power spectrum consisted of the relative power in 1 MHz bands between 6 to 14 MHz, and the total power in the 6–14 MHz band. The relative power in a particular 1 MHz band is defined as the ratio between the actual power in that band and the total power in the 6–14 MHz band. The power spectra of small cracks have larger high frequency content than do large cracks, so the ratio of high frequency power to low frequency power should be high for small cracks and low for large cracks. The relative power parameters should reflect this trend.

One additional "spatial" parameter is computed from the power spectrum. The expected value of the spatial transform is found to be an indicator of the crack size and it is a linear transformation of the power spectrum divided by the bandwidth of the spatial frequency. This ratio, in turn, is proportional to the transducer bandwidth, the viewing angle, and the velocity of ultrasound in the material (Equation 6.18). This parameter is computed by dividing the total power in the 6–14 MHz band by the spatial bandwidth.

Thus, there are a total of 10 parameters from the power spectrum—eight relative powers in 1 MHz band from 6–14 MHz, the total power in the 6–14 MHz band, and the average spatial power.

The cepstral waveform is parameterized to reflect both its shape and peak distribution because both are informative of crack size geometry. The abscissa of the cepstrum has the units of time, although it is termed "quefrency," and the locations of the peaks along the abscissa are the relevant time delays (i.e., phase information). These are a function of the viewing angle and the crack geometry.

Time delays (peaks) which are manifest beyond half the window length (of 5.12 microseconds) are artifactual. This is so because a time delay of 1 nanosecond corresponds to a crack length of 0.126 mils, and therefore a delay of 2.5 microseconds corresponded to 315 mils—which is greater than the largest crack in the sample set. Therefore, the peak distribution as well as the overall cepstral waveform shape in the 0 to 2.7 microsecond range are considered to be an appropriate interval for parameterization.

The range 0–2.7 microseconds is divided into 10 equal bands of 0.27 microsecond width and the number of local maxima as well as the area in each band are computed. Initially, the locations of all the peaks within a band of interest are computed. A local maximum is determined by that candidate peak which is greater than its three neighboring peaks. In this fashion, the total number of local maxima is computed. The area of the cepstrum in the band of interest is computed by integrating over the band.

A total of 20 parameters is computed from the cepstrum—10 relating to the area and 10 relating to the number of local maxima in to 0 to 2.7 microsecond interval.

The sine of transducer viewing angle is the final parameter.

Table 2 shows the 31 parameters that serve as candidate inputs to the ALN. Table 3 lists the character of the parameter list compiled for each experiment. Table 3 has, in addition, three items of header information: (1) the test identification number, (2) the nominal crack size, and (3) the viewing angle.

Finally, FIG. 9 is a schematic of the entire waveform preprocessing and parameterization procedures carried out for each experiment to generate the parameter list shown in Table 3. The pulse echoes collected by the transient recorder are first corrected for base line shift, gain, and damping induced by the electronic data gathering syste. The appropriate window of data is gated to isolate the region of interest (i.e., hole and crack response). The six circularly scanned waveforms and the reference waveform are then transformed into the frequency domain by an FFT algorithm.

Each of the six frequency domain signals is deconvolved from the reference signal and bandpass filtered to isolate only the frequencies of interest. The power spectrum and cepstrum are generated and the parameters extracted by the method discussed in this section.

The 31-component parameter vector, X–(x, x . . . x), is the input to the ALN.

TABLE 2
ALN INPUT PARAMETERS

| Waveform | Number | Description |
|---|---|---|
| Power Spectrum | 9 | Fractonal power in 1 MHz bands in range 6 to 14 MHz; total power |
| Spatial Power | 1 | Total power divided by width of Spatial range |
| Cepstrum | 20 | Number of T's observed in 10 equally spaced bands between 0 – 2, 700 nanoseconds; total cepstral values in the 10 bands |
| Transducer Orientation | 1 | Sin θ |
| Total:31 | | |

TABLE 3
FINAL PARAMETER LIST USED AS INPUT TO THE ALN FATIGUE CRACK MODEL

| Variable No. | Description |
|---|---|
| 1 | Test number. |
| 2 | Crack size in mils. |
| 3 | Viewing angle with respect to the normal to the plane of the crack in degrees. |
| 4 | Fractional deconvolved power in the 6–7 MHz band. |
| 5 | Fractional deconvolved power in the 7–8 MHz band. |
| 6 | Fractional deconvolved power in the 8–9 MHz band. |
| 7 | Fractional deconvolved power in the 9–10 MHz band. |
| 8 | Fractional deconvolved power in the 10–11 MHz band. |
| 9 | Fractional deconvolved power in the 11–12 MHz band. |
| 10 | Fractional deconvolved power in the 12–13 MHz band. |
| 11 | Fractional deconvolved power in the 13–14 MHz band. |
| 12 | Total deconvolved power in the 6–14 MHz band. |
| 13 | Total number of peaks in the 1–270 nanoseconds band of the cepstrum. |
| 14 | Total number of peaks in the 271–540 nanoseconds band of the cepstrum. |
| 15 | Total number of peaks in the 541–810 nanoseconds band of the cepstrum. |
| 16 | Total number of peaks in the 811–1.080 nanoseconds band of the cepstrum. |
| 17 | Total number of peaks in the 1,081–1,350 nanoseconds band of the cepstrum. |
| 18 | Total number of peaks in the 1,351–1,620 nanoseconds band of the cepstrum. |
| 19 | Total number of peaks in the 1,621–1,890 nanoseconds band of the cepstrum. |
| 20 | Total number of peaks in the 1,891–2,160 nanoseconds band of the cepstrum. |
| 21 | Total number of peaks in the 2,161–2,430 nanoseconds band of the cepstrum. |
| 22 | Total number of peaks in the 2,431–2,700 nanoseconds band of the cepstrum. |
| 23 | Area of the cepstrum in the 1–270 nanoseconds band. |
| 24 | Area of the cepstrum in the 271–540 nanoseconds band. |
| 25 | Area of the cepstrum in the 541–810 nanoseconds band. |
| 26 | Area of the cepstrum in the 811–1,080 nanoseconds band. |
| 27 | Area of the cepstrum in the 1,081–1,350 nanoseconds band. |
| 28 | Area of the cepstrum in the 1,351–1,620 nanoseconds band. |
| 29 | Area of the cepstrum in the 1,621–1,890 nanoseconds band. |
| 30 | Area of the cepstrum in the 1,891–2,160 nanoseconds band. |
| 31 | Area of the cepstrum in the 2,161–2,430 nanoseconds band. |
| 32 | Area of the cepstrum in the 2,431–2,700 nanoseconds band. |
| 33 | Total spatial power in the 6–14 MHz band. (Function of parameter 12). |
| 34 | Sine of the viewing angle. |

Each of the time signals are preprocessed and 31 parameters were computed from its power spectrum and cepstrum. The data of Series 2 (Table 4) was recorded with the transducer wedge angle at 30° to the material surface as opposed to the 20° wedge angle used in Series 1. Thus each crack specimen is recorded under two different experimental conditions and circularly scanned at six different viewing angles to yield a total of 12 time signals per specimen. The 12 time signals are treated as independent entities because, at each viewing angle, only a component of the plane of the crack is perpendicular to the longitudinal axis of the transducer—the largest component corresponding to the case when the viewing angle is perpendicular to the plane of the crack and it is equal to the nominal crack length, so a total of 192 time signals (16 cracks × 12 signals/crack), each of which contains 512 points sampled at 10 nanoseconds/point, are parameterized to produce a data base consisting of 192 records with 31 independent parameters. The 32nd variable is the dependent variable, $l$ = crack length.

For purposes of modeling, the 192 data set is divided into three groups—the fitting, selection, and evaluation subsets. Table 4 shows the distribution of data in the three subsets. The fitting and selection subset each consist of 72 records of 12 crack specimens from either Series 1 or Series 2. The evaluation subset consists of 48 records from four specimen cracks—192 mils, 93 mils, 39 mils and 14 mils. The fitting and selection subsets of data are used to synthesize the model to measure crack length and the evaluation subset is used to infer its generalizing capabilities to new crack specimens that have not been used in designing the model.

TABLE 4
DISTRIBUTION OF THE 192 DATA RECORDS AMONG THE THREE DATA SUBSETS

| | DATA SUBSET | | |
|---|---|---|---|
| Specimen | Fitting | Selection | Evaluation |
| 15–279 | 6 (I) | 6 (II) | |
| 14–192 | | | 6 (I), 6 (II) |
| 13–150 | 6 (II) | 6 (I) | |
| 12–113 | 6 (I) | 6 (II) | |
| 11–093 | | | 6 (I), 6 (II) |
| 10–073 | 6 (II) | 6 (I) | |
| 09–054 | 6 (I) | 6 (II) | |
| 08–048 | 6 (II) | 6 (I) | |
| 07–039 | | | 6 (I), 6 (II) |
| 06–027 | 6 (I) | 6 (II) | |
| 05–022 | 6 (II) | 6 (I) | |
| 04–018 | 6 (I) | 6 (II) | |
| 03–014 | | | 6 (I), 6 (II) |
| 02–011 | 6 (II) | 6 (I) | |
| 01–000 | 6 (I) | 6 (II) | |
| 00–000 | 6 (II) | 6 (I) | |
| TOTAL RECORDS | 72 | 72 | 48 |

I - Series 1 Records
II - Series 2 Records

By design, most of the crack sample specimens are in the smaller size range (50 percent of them were below 48 mils) because accuracy in this range is of prime importance. Therefore, it is the goal to create a model that can discriminate between smaller sized cracks between than between larger sized cracks.

One way to implement this bias is to train the model to measure the logarithm of the crack length, rather than the crack length itself. The log function has the desirable property of rapid changes for small values of the argument because its derivative is inversely proportional to $l$. However, these changes occur near 0 mils, where the derivative is infinite, whereas the model's requirement calls for rapid changes at a higher value—such as 30 mils. consequently, it was decided to train the model to measure $y$, where:

$$y = \text{Ln}\left(\frac{l'}{30}\right) \quad (8.1)$$

and, $$l' = l(1-\sin\theta) \quad (8.2)$$

where
$l$ = nominal crack length in mils
$\theta$ = transducer viewing angle in degrees Equation (8.1) is a function of the transducer viewing angle $\theta$ as well as $l$. It is assumed that the crack length "visible" to the transducer is proportional to (1-sin $\theta$); hence, Equation 8.2.

FIG. 10(a) outlines the model synthesis procedure. It shows a plot of $y$ (from Equation 8.1) versus crack length $l$. Notice that the crossover point is $l = 30$ for a 0° viewing angle. The crossover point increases for increases in viewing angle. The slope of Equation 8.1 is $$\frac{\delta y}{\delta l} = 1/l \tag{8.3}$$

which is large for small values of $l$ and progressively decreases for increases in crack length $l$. It effectively penalizes the model for small errors in the range (0–30 mils), where a model output could be in error by several percentage points from its nominal value, whereas the corresponding error in the larger range (30 mils and above) is not so severely penalized.

It must be stressed that the model is trained to recognize a function of the nominally characterized crack length. The agreement between nominally characterized crack lengths and actual crack lengths can only be verified by destructively testing the sample specimens.

After model synthesis, the estimate for new (i.e., previously unseen) data is processed through an inverse function of Equations (8.1) and (8.2) to yield the estimated measured crack size,[1/] i.e., $$\hat{l} = \frac{30 \, e^{\hat{y}}}{(1 - \sin\theta)} \tag{8.4}$$

where
$\hat{y}$ = estimate computed by the ALN
$\hat{l}$ = measured crack length obtained from $\hat{y}$
$\theta$ = viewing angle.

[1/]The carat above a variable (e.g., $\hat{y}$) denotes an estimated quantative FIG. 10(b) shows how $\hat{l}$ is obtained. The relevant 31 parameters are computed by the methods described above and are input to the ALN. Its output, $y$, is processed through a system which realizes Equation 8.4, thereby producing the measured crack size, $\hat{l}$. If data of the same unknown crack are available at different viewing angles, additional measurements of the crack can be made. These measurements can be combined (by averaging, for example) to yeild a composite measurement of the crack length. Therefore, the composite crack length estimate for a given fastener hole, $\hat{l}_c$ is is the average of the six ALN model outputs for each of the size viewing angles:

$$\hat{l} = 1/6 \, \hat{l}(\theta = 0°) + \hat{l}(\theta = 5.5°) + \hat{l}(\theta = 11°) + \hat{l}(\theta = 16.5°) + \hat{l}(\theta = 22°) + \hat{l}(\theta = 27.5°) \tag{8.5}$$

An ALN is trained via the methods summarized above using the data from the 12 sample crack specimens (Table 4) and the parameters described above.

The data from the 12 crack specimens consist of 144 vectors in the 31-parameter space. The model output variable, $y$, is the function realized by Equation (8.1). Thus the information used for each experiment is:

Input variables—31 parameters of the recorded pulse echo in Table 2.

Output variable—a function of the crack length as per Equation 8.1.

It is significant that the characteristics of the transducer and the material are not used—indeed one of the purposes of the waveform preprocessing step is to remove their effects as much as possible.

The fitting and selection data subsets (Table 4) are used to train the ALN model. In this exercise, the output variable is used for model synthesis. After the model is obtained, the evaluation subset is input to the model to test its ability to infer crack length for data not previous used.

The synthesized ALN model is shown in FIG. 11(a). The four layered network realizes a multinomial (i.e., a polynomial in more than two variables) of up to order 16 in the selected input parameters. It can be seen that 16 of the 31 candidate input parameters were found to contain information relative to crack length.

The ALN model of FIG. 11(a) is well known in the prior art and will not be further discussed herein. The ALN is fully described in *Cybernetics and the Management of Ecological Systems*, Robinson (Ed.), Spartan Books, New York, 1972, in an article of A. N. Mucciardi entitled "Neuromine Nets as the Basis for the Predictive Component of Robot Brains," pp. 159-193.

Among the 16 parameters that were selected, the more important ones include the fractional power in the 10-11 MHz band, the cepstral area in the 1-270 nanosecond range, and the total power in the 6-14 MHz range. The first and last mentioned substantiate in part the theoretical findings above that power in the reflected signal is proportional to the crack length. Of course, theory points to a linear relationship between them, whereas the actual analytical relationship is nonlinear.

Table 5 and FIG. 11(b) show the performance of the ALN classifier in measuring subsurface fatigue cracks. The mean absolute percentage error, which is a measure of how close the model's output is to the nominal crack length, i.e., $$e = \left|\frac{l - \hat{l}}{l}\right| \times 100\% \tag{8.6}$$

is 33.4 percent for both Series 1 and Series 2. If the average of the two estimates from Series 1 and 2 is computed (last column in Table 5), the mean absolute percentage error is 30.3 percent. The largest errors are committed in classifying a 14 mil crack in Series 1, a 39 mil crack and a 93 mil crack in Series 2.

TABLE 5

PERFORMANCE OF ALN MODEL IN MEASURING CRACK SIZE FROM ULTRASONIC NDE WAVEFORM PARAMETERS

| True Crack Length l (mils) | Series 1 | | Series 2 | | Average of Series 1 & 2 | |
|---|---|---|---|---|---|---|
| | Estimated Length l | Percent Error | Estimated Length l | Percent Error | Estimated Length l | Percent Error |
| 279 | 278.7 | 0.1 | 311.7 | −11.7 | 295.2 | −5.8 |
| 192 | 178.6 | 7.0 | 159.6 | 16.9 | 169.1 | 11.9 |
| 150 | 137.3 | 8.5 | 122.6 | 18.3 | 130.0 | 13.4 |
| 113 | 84.5 | 25.2 | 81.8 | 27.6 | 83.2 | 26.4 |
| 93 | 75.6 | 18.7 | 26.4 | 71.6 | 51.0 | 45.2 |
| 73 | 48.6 | 33.4 | 34.8 | 52.3 | 41.7 | 42.9 |

TABLE 5-continued

PERFORMANCE OF ALN MODEL IN MEASURING
CRACK SIZE FROM ULTRASONIC NDE WAVEFORM PARAMETERS

| True Crack Length 1 (mils) | Series 1 | | Series 2 | | Average of Series 1 & 2 | |
|---|---|---|---|---|---|---|
| | Estimated Length 1 | Percent Error | Estimated Length 1 | Percent Error | Estimated Length 1 | Percent Error |
| 54 | 56.6 | −4.8 | 64.9 | −20.2 | 60.8 | −12.5 |
| 48 | 30.4 | 36.7 | 43.2 | 10.0 | 36.8 | 23.3 |
| 39 | 40.3 | −3.3 | 96.7 | −147.4 | 68.5 | −75.6 |
| 27 | 47.3 | 75.2 | 20.0 | 25.9 | 33.7 | −24.6 |
| 22 | 21.5 | −2.3 | 18.4 | 16.4 | 20.0 | 9.3 |
| 18 | 18.7 | −3.9 | 21.6 | −20.0 | 20.2 | −11.9 |
| 14 | 42.6 | 204.3 | 11.5 | 17.9 | 27.1 | −93.2 |
| 11 | 15.9 | 44.5 | 12.2 | −10.9 | 14.1 | −27.7 |
| 0 | 3.8 | — | 5.3 | — | 4.6 | — |
| 0 | 5.5 | — | 17.7 | — | 11.6 | — |
| | Mean % Error: 31.4 Mean Absolute 33.4 % Error: | | Mean % Error: 3.3 Mean Absolute 33.4 % Error: | | Mean % Error: −5.6 Mean Absolute 30.3 % Error: | |

One measure of robustness of any mathematical model is determined by its sensitivity to changes in the input parameters. Table 5 shows the measured crack length sensitivity to a 1 percent change in the input NDE parameters. The table is a rank ordering of the most to least sensitive parameters. The sensitivity for each variable $x_i$, is computed by calculating the change in model output for small perturbations of the input variable from its nominal value. All other input variables are kept constant. For example, if parameter $x_{30}$, which is the cepstral area between 1891–2160 nanoseconds, changes by +1 percent of its range, the estimated crack length changes by 3.19 percent, or 2.87 mils from its nominal value. If the sine of the viewing angle (parameter $x_{34}$) changes by +1 percent of its range, the estimated crack length changes by only −0.08 percent, or −0.07 mils, from its nominal value. The conclusion from these results is that parameter $x_{30}$, the cepstral area between 1891–2160 nanoseconds, is more critical than the sine of the viewing angle, $x_{34}$. From a practical viewpoint, this is a highly desirable result since very accurate angular measurements are not predicted to be necessary for accurate crack estimates using this system.

Another important function of a robust mathematical model is the agreement between its empirically implemented input relationship and the underlying physical phenomena. Examining the table, parameters $x_8$, $x_{23}$, and $x_{10}$, the fractional power in the 10–11 MHz range, cepstral area in the 1–270 nanoseconds interval, and the fractional power in the 12–13 MHz band, respectively, have been negtively correlated to the crack length by the model. It is known from physical principals that the power spectra of the reflected signals from large and small cracks differ in that the former has higher low frequency content than in the latter. At the frequencies 10–13 MHz, the wavelength varies from 12.6 mils to 9.7 mils which is too small to interact with large cracks (279 mils, etc.) Thus, any increase in the energy content in these bands is an indication of a smaller crack. The sensitivity table indicates the same trend—a 1 percent increase in parameters $x_8$ and $x_{10}$, leads to 0.29 mil and 0.17 mil decrease in crack length. An increase in cepstral area in the 1–270 nanosecond region ($x_{23}$) is an indication of increase in the time delays due to small cracks in the 0–34 mil range. Therefore, larger cracks will have a smaller value of $x_{23}$. The sensitivity table indicates the same trend. A one percent increase in $x_{23}$ causes a 0.21 mil decrease in the estimated crack length.

TABLE 6

CRACK LENGTH SENSITIVITY TO CHANGES
IN NDE ULTRASONIC PARAMETERS

| Variable Name* (Xi) | Average Crack Length Change Per 1% Change In Variable Xi | |
|---|---|---|
| | MILS | % |
| Cepstral area: 1891–2160 nsec band ($X_{30}$) | 2.87 | 3.19 |
| Total power: 6–14 MHz band ($X_{12}$) | 1.44 | 1.60 |
| Cepstral area: 2161–2430 nsec band ($X_{31}$) | 1.10 | 1.23 |
| Cepstral area: 271–540 nsec band ($X_{24}$) | 0.33 | 0.36 |
| Cepstral area: 811–1080 nsec band ($X_{26}$) | 0.32 | 0.35 |
| Fractional power: 10–11 MHz band ($X_8$) | −0.29 | −0.33 |
| Cepstral area: 1–270 nsec band ($X_{23}$) | −0.21 | −0.23 |
| Cepstral peaks: 811–1080 nsec band ($X_{16}$) | 0.18 | 0.20 |
| Fractional power: 12–13 MHz band ($X_{10}$) | −0.17 | −0.19 |
| Cepstral area: 1351–1620 nsec band ($X_{28}$) | 0.09 | 0.10 |
| Sine of viewing angle ($X_{34}$) | −0.07 | −0.08 |
| Cepstral peaks: 1621–1890 nsec band ($X_{19}$) | 0.05 | 0.06 |
| Cepstral area: 2431–2700 nsec band ($X_{32}$) | −0.02 | −0.03 |
| Cepstral peaks: 2431–2700 nsec band ($X_{22}$) | 0.02 | 0.02 |
| Cepstral peaks: 1081–1350 nsec band ($X_{17}$) | −0.01 | −0.02 |
| Fractional power: 13–14 MHz band ($X_{11}$) | 0.01 | 0.01 |

*Power Spectrum and Cepstrum have been deconvolved and band-pass filtered
$l = ct = (0.126$ mils/nsec$) t$

| Δt, nsec | Δl, mils |
|---|---|
| 1–270 | 0.1–34 |
| 271–540 | 34–68 |
| 811–1,080 | 102–136 |
| 1,081–1,350 | 136–170 |
| 1,351–1,620 | 170–204 |
| 1,621–1,890 | 204–238 |
| 1,891–2,160 | 238–272 |
| 2,161–2,430 | 272–306 |

TABLE 6-continued

CRACK LENGTH SENSITIVITY TO CHANGES
IN NDE ULTRASONIC PARAMETERS

| Variable Name* (Xi) | Average Crack Length Change Per 1% Change In Variable Xi | |
|---|---|---|
| | MILS | % |
| 2,431–2,000 | 306–340 | |

Finally, parameters $x_{30}$, $x_{12}$ and $x_{31}$ which are the cepstral area in 1891–2160 nanoseconds region, the total power in the 6–14 MHz band and the cepstral area in the 2161–2430 nanosecond band, respectively, have been positively correlated with the crack length by the model. Parameter $x_{12}$, the total power reflected from a crack, is known to increase with increase in crack length and in, previous investigations, was the sole indicator of crack length. Parameters $x_{30}$ and $x_{31}$ are time delays associated with cracks ranging from 238–306 mils. An increase in these values is an indication of a large crack. The crack length increases by an estimated 2.87 mils and 1.10 mils for 1 percent changes in $x_{30}$ and $x_{31}$, respectively.

What is claimed is:

1. A system for measurement of surface and subsurface material flaw size which comprises,
   a. means for obtaining data as a function of a flaw in a medium,
   b. means to perform spectral analysis on said data,
   c. means to perform a cepstral analysis on said data,
   d. means responsive to the output of both (b) and (c) to provide a set of parameters; and
   e. means responsive to predetermined ones of said parameters to provide an estimated flaw length indication.

2. A system as set forth in claim 1, wherein said means in (a) is an acoustic means and said data is an analog function of time and angle between said acoustic means and a flaw under test.

3. A system as set forth in claim 2 further including means to digitally store said data from (a).

4. A system as set forth in claim 3 further including manipulator means coupled to said means to store for eliminating acoustic characteristics in said stored data.

5. A system as set forth in claim 4, wherein said manipulator means includes means to take a Fourier transform of said stored data and reference data, means to take a deconvolution of said Fourier transforms and means to take an inverse Fourier transform of said deconvolution.

6. A system as set forth in claim 5, wherein said means in (b) includes means to take a Fourier transform and said means in (c) includes means to take a natural logarithm and means to take a Fourier transform of said natural logarithm.

7. A system as set forth in claim 6, wherein said acoustic means is a plurality of ultrasonic transducers.

8. A system as set forth in claim 7, wherein said means in (e) is an adaptive learning network.

9. A system as set forth in claim 6, wherein said means in (e) is an adaptive learning network.

10. A system as set forth in claim 5, wherein said means in (e) is an adaptive learning network.

11. A system as set forth in claim 4, wherein said means in (b) includes means to take a Fourier transform and said means in (c) includes means to take a natural logarithm and means to take a Fourier transform of said natural logarithm.

12. A system as set forth in claim 4, wherein said means in (e) is an adaptive learning network.

13. A system as set forth in claim 3, wherein said means in (b) includes means to take a Fourier transform and said means in (c) includes means to take a natural logarithm and means to take a Fourier transform of said natural logarithm.

14. A system as set forth in claim 3, wherein said means in (e) is an adaptive learning network.

15. A system as set forth in claim 2, wherein said means in (b) includes means to take a Fourier transform and said means in (c) includes means to take a natural logarithm and means to take a Fourier transform of said natural logarithm.

16. A system as set forth in claim 2, wherein said acoustic means is a plurality of ultrasonic transducers.

17. A system as set forth in claim 1 further including means to digitally store said data from (a).

18. A system as set forth in claim 17 further including manipulator means coupled to said means to store for eliminating acoustic characteristics in said stored data.

19. A system as set forth in claim 18, wherein said manipulator means includes means to take a Fourier transform of said stored data and reference data, means to take a deconvolution of said Fourier transforms and means to take an inverse Fourier transform of said deconvolution.

20. A system as set forth in claim 19, wherein said means in (b) includes means to take a Fourier transform and said means in (c) includes means to take a natural logarithm and means to take a Fourier transform of said natural logarithm.

21. A system as set forth in claim 18, wherein said means in (b) includes means to take a Fourier transform and said means in (c) includes means to take a natural logarithm and means to take a Fourier transform of said natural logarithm.

22. A system as set forth in claim 3, wherein said means in (b) includes means to take a Fourier transform and said means in (c) includes means to take a natural logarithm and means to take a Fourier transform of said natural logarithm.

23. A system as set forth in claim 1, wherein said means in (b) includes means to take a Fourier transform and said means in (c) includes means to take a natural logarithm and means to take a Fourier transform of said natural logarithm.

24. A system as set forth in claim 1, wherein said means in (e) is an adaptive learning network.

* * * * *